(12) United States Patent
Hen

(10) Patent No.: US 12,564,405 B2
(45) Date of Patent: Mar. 3, 2026

(54) BLOOD VESSEL COMPRESSION SYSTEMS

(71) Applicant: DREAMEDIC LTD., Alon Hagalil (IL)

(72) Inventor: Assaf Hen, Alon Hagalil (IL)

(73) Assignee: DREAMEDIC LTD., Alon Hagalil (IL)

( * ) Notice: Subject to any disclaimer, the term of this patent is extended or adjusted under 35 U.S.C. 154(b) by 288 days.

(21) Appl. No.: 18/277,293

(22) PCT Filed: Feb. 16, 2022

(86) PCT No.: PCT/IL2022/050185
§ 371 (c)(1),
(2) Date: Aug. 15, 2023

(87) PCT Pub. No.: WO2022/175946
PCT Pub. Date: Aug. 25, 2022

(65) Prior Publication Data
US 2024/0138842 A1 May 2, 2024

Related U.S. Application Data

(60) Provisional application No. 63/150,102, filed on Feb. 17, 2021.

(51) Int. Cl.
*A61B 17/12* (2006.01)
*A61B 17/00* (2006.01)

(52) U.S. Cl.
CPC .. *A61B 17/12009* (2013.01); *A61B 17/12109* (2013.01); *A61B 17/12136* (2013.01); *A61B 2017/00867* (2013.01); *A61B 2017/12004* (2013.01)

(58) Field of Classification Search
CPC ........ A61B 17/12109; A61B 17/12013; A61B 17/12009; A61B 17/12136; A61B 2017/00557; A61B 2017/00867; A61B 2017/3407; A61B 17/3403; A61B 17/132; A61B 17/1322; A61B 17/135; A61B 17/1325
See application file for complete search history.

(56) References Cited

U.S. PATENT DOCUMENTS

| | | | |
|---|---|---|---|
| 5,722,981 | A | 3/1998 | Stevens |
| 2009/0264905 | A1* | 10/2009 | Funada .................. A61B 17/04 |
| | | | 606/144 |
| 2016/0302793 | A1* | 10/2016 | Fung .................. A61B 17/0487 |
| 2019/0192164 | A1 | 6/2019 | Parekh et al. |

FOREIGN PATENT DOCUMENTS

WO        2005055837 A1      6/2005

OTHER PUBLICATIONS

Klein et al., (2019) Emerging Therapies for Prehospital Control of Hemorrhage. Journal of Surgical Research; Accepted Sep. 23, 2019; pp. 1-9 (9 pages).
McCracken et al., (2022) A review of two emerging technologies for pre-hospital treatment of non-compressible abdominal hemorrhage. Transfusion 62(Suppl 1): S313-S322 (10 pages).

* cited by examiner

*Primary Examiner* — Thomas McEvoy
(74) *Attorney, Agent, or Firm* — Roach Brown McCarthy & Gruber, P.C.; Kevin D. McCarthy

(57) ABSTRACT

The present invention relates to a blood vessel compression system that includes blood vessel compression assemblies and apparatus for the insertion thereof.

18 Claims, 24 Drawing Sheets

BLOOD VESSEL COMPRESSION SYSTEMS

FIELD OF THE INVENTION

The present invention relates to a blood vessel compression system that includes blood vessel compression assemblies and apparatus for the insertion thereof.

BACKGROUND OF THE INVENTION

Non-compressible abdominal wound hemorrhage is a frequent cause of morbidity and mortality worldwide. Treatment procedures of such wounds usually require surgical intervention and cannot be applied at the site of injury, such as a battlefield or a road traffic accident. Early and effective hemorrhage control can save more lives than any other measure.

While a wide variety of tourniquets or clamping may be used to apply pressure to wounds to the extremities, such solutions are ineffective in abdominal wounds. Internal bleeding and organ damage require occlusion of the abdominal descending aorta to cut-off the blood supply to the non-compressible arterial hemorrhage. Simple application of an unfocused external force applied on the surface of the body is inadequate as the pressure usually will not reach the internal wound and will be ineffective in reduction or occlusion of blood flow through the descending aorta proximal to the bifurcation in the abdomen, due to the deep location of the aorta in the body. Accordingly, there is an ongoing need for portable devices that may be rapidly applied in the field, which are capable of restrict blood flow through the descending aorta.

SUMMARY OF THE INVENTION

The present disclosure is directed toward an insertion device configured to penetrate a patient's body through the back, and to create a working space in front of the abdominal aorta, and to blood vessel compression apparatus that includes the insertion device and a compression assembly provided with components that can be extended into the working space created by the insertion device, and operable to press against the abdominal aorta, and optionally the inferior vena cava, so as to obstruct blood flow therethrough.

According to an aspect of the invention, there is provided an insertion device comprising a base plate, at least one introducer shaft, at least one guide member, a push member, at least one push shaft and a handle assembly. The base plate comprises at least one base plate opening. The at least one introducer shaft is axially movable through the base plate openings, wherein the introducer shaft defines an introducer shaft lumen and comprises a sharp distal end. The at least one guide member is affixed to the base plate and extends proximally therefrom. The push member is axially slidable over the at least one guide member.

The at least one push shaft is axially movable through the introducer shaft lumen. The at least one push shaft comprises an atraumatic distal end. At least one of the at least one push shafts defines a push shaft lumen and comprises a side opening which is proximal to the atraumatic distal end. The handle assembly is coupled to the push member, and comprises a first stage handle and a second stage handle, wherein the first stage handle is coupled to the second stage handle. The at least one introducer shaft is attached to the push member and is axially movable therewith. The at least one push shaft is attached to the second stage handle and is axially movable therewith. The at least one push shaft is movable between a retained position, in which the atraumatic distal end is retained within the introducer shaft lumens, and a pushed position, in which the atraumatic distal end protrudes distally from the sharp distal ends.

In some embodiments, the base plate further comprises a tongue extending downwardly and distally at a lower end of the base plate.

In some embodiments, the push member comprises at least one guide channel, and wherein each guide member extends through a corresponding guide channel.

In some embodiments, the push member comprises at least one plate.

In some embodiments, the at least one plate comprises at least two plates, attached to each other via at least one push support extension.

In some embodiments, the insertion device further comprises at least one stopper coupled to the at least one guide member, and configured to prevent axial advancement of the push member along the at least one guide member beyond the at least one stopper.

In some embodiments, the at least one stopper comprises a slidable member that can transition between a released state, during which it can slide along the guide member, and a locked state, in which it is secured to the guide member.

In some embodiments, the at least one stopper further comprises a side opening and a compression bolt configured to be threaded through the side opening and lock the stopper against the guide member, thereby transitioning it to the locked state.

In some embodiments, the at least one stopper is a frame defining four stopper channels at its corners, and wherein the at least one guide member comprises four guide members extending through the stopper channels.

In some embodiments, the at least one guide member comprises at least one guide member side opening, and wherein the at least one stopper comprises an elongated pin insertable into the at least one guide member side opening.

In some embodiments, the at least one guide member side opening comprises a plurality of guide member side openings which are axially spaced from each other.

In some embodiments, the at least one guide member side opening comprises a plurality of guide member side openings which are axially spaced from each other.

In some embodiments, the at least one threaded guide member side opening comprises a plurality of threaded guide member side openings which are axially spaced from each other.

In some embodiments, the at least one stopper comprises a cam hinged to the at least one guide member by a central hinge, wherein the cam comprises a lobe having an outer edge following varying distances from the central hinge along the circumference thereof.

In some embodiments, the at least one guide member comprises markings thereon.

In some embodiments, the first stage handle is rotatably coupled to the second stage handle.

In some embodiments, the first stage handle is releasably coupled to the second stage handle.

In some embodiments, the insertion device further comprises two brackets attached to the push member and extending therefrom.

In some embodiments, each bracket comprises a curved rail, and wherein the first stage handle comprises two side extensions, each side extensions comprising a guide projection which is slidably movable within a corresponding curved rail.

In some embodiments, each curved rail is open ended at an end thereof, and wherein the first stage handle is releasable from the brackets by sliding the guide projections out of the open ended curved rails.

In some embodiments, the first stage handle comprises a clip, and wherein the second stage handle comprises a second handle main body to which the clip is attached.

In some embodiments, the second handle main body comprises a coupling recess with which the clip is engaged.

In some embodiments, the clip is C-shaped.

In some embodiments, the second stage handle comprises two locking arms configured to engage with the brackets.

In some embodiments, the locking arms are configured to be releasable coupled to the brackets.

In some embodiments, each bracket comprises a locking socket, and wherein each locking arm comprises a locking arm projection configured to lock into the corresponding locking socket.

In some embodiments, the at least one base plate opening comprises two base plate openings which are laterally spaced from each other, the at least one introducer shaft comprises two introducer shafts, and the at least one push shaft comprises two push shafts.

In some embodiments, the lateral distance between both introducer shafts 120 is at least 5 centimeters.

In some embodiments, the lateral distance between both introducer shafts 120 is at least 10 centimeters.

In some embodiments, both introducer shafts are laterally aligned.

In some embodiments, there is provided a blood vessel compression apparatus comprising the insertion device and a compression assembly that comprises a wire and a wire retrieval assembly. The wire retrieval assembly comprises a snare loop configured to transition between a compressed state and an expanded state. The push shafts comprise a first push shaft and a second push shaft. The first push shaft defines a first push shaft lumen and comprises a first side opening. The second push shaft defines a second push shaft lumen and comprises a second push shaft side opening. The wire extends at least partially through the second push shaft lumen. The wire retrieval assembly extends at least partially through the first push shaft lumen.

In some embodiments, the wire retrieval assembly further comprises a longitudinal portion extending proximally from the snare loop, and movable axially within the first push shaft lumen.

In some embodiments, the longitudinal portion is configurated to extend proximally out of the first push shaft, and comprises a retrieval proximal stopping portion disposed proximal to the second stage handle. The retrieval proximal stopping portion is sized to be larger than the first push shaft lumen.

In some embodiments, the first side opening is facing upward or downward with respect to a longitudinal axis defined by the first push shaft In some embodiments, the first side opening comprises two opposing openings, one facing upward and the other facing downward with respect to a longitudinal axis defined by the first push shaft.

In some embodiments, the snare loop comprises a shape memory material and is pre-shaped to self-expand through the first side opening.

In some embodiments, the wire comprises a shape memory material and is pre-shaped to bend sideways from the second push shaft lumen through the second side opening, toward the first push shaft.

In some embodiments, a distal end of the wire comprises a round bead.

In some embodiments, the blood vessel compression apparatus further comprises a rotating handle attached to the base plate, wherein the rotating handle is configured to transition between a folded state and an extended state.

In some embodiments, at least one component of the insertion device, selected from any one of: the introducer shafts, the push shafts, the stopper, the introducers push member, and/or the handle assembly, is removable from the remainder of the blood vessel compression apparatus.

In some embodiments, there is provided a blood vessel compression apparatus comprising the insertion device and a compression assembly that comprises a balloon assembly. The balloon assembly comprises two balloon catheters, each defining a balloon catheter lumen, and two inflatable balloons, each inflatable balloon attached to one balloon catheters. Each of both push shafts comprises a push shaft lumen and a corresponding side opening. Each balloon catheter extends at least partially through push shaft lumen of the corresponding push shaft.

In some embodiments, the compression assembly further comprises a fluid source which is in fluid communication with the at least one balloon catheter.

In some embodiments, the balloon catheters comprise shape memory materials, and are pre-shaped to bend sideways through the side opening of the corresponding push shafts.

In some embodiments, the balloon assembly further comprises at least one catheter proximal stopping portion attached to a proximal portion of the at least one of the balloon catheters. The at least one catheter proximal stopping portion is disposed proximal to the second stage handle, and is sized to be larger than the corresponding push shaft lumen.

In some embodiments, the side openings of both push shafts are facing each other at a non-zero angle.

In some embodiments, the balloon assembly further comprises at least one unidirectional valve in fluid communication with at least one of the balloon catheter lumens, configured to allow fluid flow in a distally oriented direction through the at least one balloon catheter lumen, and prevent backflow therethrough in a proximally oriented direction.

In some embodiments, there is provided a blood vessel compression apparatus comprising the insertion device and a compression assembly that comprises a balloon assembly, wherein the at least one base plate opening comprises a single plate opening, wherein the at least one introducer shaft comprises a single introducer shaft, wherein the at least one push shaft comprises a single push shaft, wherein the balloon assembly comprises a single balloon catheter which defines a balloon catheter lumen, and an inflatable balloon attached to the balloon catheter, and wherein each balloon catheter extends at least partially through the push shaft lumen.

In some embodiments, the compression assembly further comprises a fluid source which is in fluid communication with the balloon catheter.

In some embodiments, the balloon catheter comprises a shape memory material, and is pre-shaped to bend sideways through the side opening of the push shaft.

In some embodiments, the balloon assembly further comprises a unidirectional valve in fluid communication with the balloon catheter lumen, configured to allow fluid flow in a distally oriented direction through the balloon catheter lumen, and prevent backflow therethrough in a proximally oriented direction.

According to another aspect of the invention, there is provided an insertion device comprising a base plate, two introducer shafts, at least one guide member, a push member, two push shafts and a handle assembly. The base plate comprises two base plate openings which are laterally spaced from each other. The introducer shafts are axially movable through the base plate openings, wherein each introducer shaft defines an introducer shaft lumen and comprises a sharp distal end. The at least one guide member is affixed to the base plate and extends proximally therefrom. The push member is axially slidable over the at least one guide member.

The push shafts are axially movable through the introducer shaft lumens. Each push shaft comprises an atraumatic distal end. At least one of the push shafts defines a push shaft lumen and comprises a side opening which is proximal to the atraumatic distal end. The handle assembly is coupled to the push member, and comprises a first stage handle and a second stage handle, wherein the first stage handle is coupled to the second stage handle. Both introducer shafts are attached to the push member and are axially movable therewith. Both push shafts are attached to the second stage handle and are axially movable therewith. The push shafts are movable between a retained position, in which the atraumatic distal ends are retained within the introducer shaft lumens, and a pushed position, in which the atraumatic distal ends protrude distally from the sharp distal ends.

In some embodiments, the base plate further comprises a tongue extending downwardly and distally at a lower end of the base plate.

In some embodiments, the lateral distance between both introducer shafts 120 is at least 5 centimeters.

In some embodiments, the lateral distance between both introducer shafts 120 is at least 10 centimeters.

In some embodiments, both introducer shafts are laterally aligned.

In some embodiments, the push member comprises at least one guide channel, and wherein each guide member extends through a corresponding guide channel.

In some embodiments, the push member comprises at least one plate.

In some embodiments, the at least one plate comprises at least two plates, attached to each other via at least one push support extension.

In some embodiments, the insertion device further comprises at least one stopper coupled to the at least one guide member, and configured to prevent axial advancement of the push member along the at least one guide member beyond the at least one stopper.

In some embodiments, the at least one stopper comprises a slidable member that can transition between a released state, during which it can slide along the guide member, and a locked state, in which it is secured to the guide member.

In some embodiments, the at least one stopper further comprises a side opening and a compression bolt configured to be threaded through the side opening and lock the stopper against the guide member, thereby transitioning it to the locked state.

In some embodiments, the at least one stopper is a frame defining four stopper channels at its corners, and wherein the at least one guide member comprises four guide members extending through the stopper channels.

In some embodiments, the at least one guide member comprises at least one guide member side opening, and wherein the at least one stopper comprises an elongated pin insertable into the at least one guide member side opening.

In some embodiments, the at least one guide member side opening comprises a plurality of guide member side openings which are axially spaced from each other.

In some embodiments, the at least one guide member side opening comprises a plurality of guide member side openings which are axially spaced from each other.

In some embodiments, the at least one threaded guide member side opening comprises a plurality of threaded guide member side openings which are axially spaced from each other.

In some embodiments, the at least one stopper comprises a cam hinged to the at least one guide member by a central hinge, wherein the cam comprises a lobe having an outer edge following varying distances from the central hinge along the circumference thereof.

In some embodiments, the at least one guide member comprises markings thereon.

In some embodiments, the first stage handle is rotatably coupled to the second stage handle.

In some embodiments, the first stage handle is releasably coupled to the second stage handle.

In some embodiments, the insertion device further comprises two brackets attached to the push member and extending therefrom.

In some embodiments, each bracket comprises a curved rail, and wherein the first stage handle comprises two side extensions, each side extensions comprising a guide projection which is slidably movable within a corresponding curved rail.

In some embodiments, each curved rail is open ended at an end thereof, and wherein the first stage handle is releasable from the brackets by sliding the guide projections out of the open ended curved rails.

In some embodiments, the first stage handle comprises a clip, and wherein the second stage handle comprises a second handle main body to which the clip is attached.

In some embodiments, the second handle main body comprises a coupling recess with which the clip is engaged.

In some embodiments, the clip is C-shaped.

In some embodiments, the second stage handle comprises two locking arms configured to engage with the brackets.

In some embodiments, the locking arms are configured to be releasable coupled to the brackets.

In some embodiments, each bracket comprises a locking socket, and wherein each locking arm comprises a locking arm projection configured to lock into the corresponding locking socket.

In some embodiments, there is provided a blood vessel compression apparatus comprising the insertion device and a compression assembly that comprises a wire and a wire retrieval assembly. The wire retrieval assembly comprises a snare loop configured to transition between a compressed state and an expanded state. The push shafts comprise a first push shaft and a second push shaft. The first push shaft defines a first push shaft lumen and comprises a first side opening. The second push shaft defines a second push shaft lumen and comprises a second push shaft side opening. The wire extends at least partially through the second push shaft lumen. The wire retrieval assembly extends at least partially through the first push shaft lumen.

In some embodiments, the wire retrieval assembly further comprises a longitudinal portion extending proximally from the snare loop, and movable axially within the first push shaft lumen.

In some embodiments, the longitudinal portion is configured to extend proximally out of the first push shaft, and comprises a retrieval proximal stopping portion disposed proximal to the second stage handle. The retrieval proximal stopping portion is sized to be larger than the first push shaft lumen.

In some embodiments, the first side opening is facing upward or downward with respect to a longitudinal axis defined by the first push shaft In some embodiments, the first side opening comprises two opposing openings, one facing upward and the other facing downward with respect to a longitudinal axis defined by the first push shaft.

In some embodiments, the snare loop comprises a shape memory material and is pre-shaped to self-expand through the first side opening.

In some embodiments, the wire comprises a shape memory material and is pre-shaped to bend sideways from the second push shaft lumen through the second side opening, toward the first push shaft.

In some embodiments, a distal end of the wire comprises a round bead.

In some embodiments, there is provided a blood vessel compression apparatus comprising the insertion device and a compression assembly that comprises a balloon assembly. The balloon assembly comprises at least one balloon catheter defining a balloon catheter lumen, and at least one inflatable balloon attached to the at least one balloon catheter. The at least one balloon catheter extends at least partially through the push shaft lumen of the at least one push shaft.

In some embodiments, the compression assembly further comprises a fluid source which is in fluid communication with the at least one balloon catheter.

In some embodiments, the at least one balloon catheter comprises a shape memory materials, and is pre-shaped to bend sideways through the side opening of the corresponding push shaft.

In some embodiments, the balloon assembly further comprises at least one catheter proximal stopping portion attached to a proximal portion of the at least one balloon catheter. The catheter proximal stopping portion is disposed proximal to the second stage handle, and is sized to be larger than the corresponding push shaft lumen.

In some embodiments, each of the two push shafts defines a push shaft lumen and comprises a side opening. The at least one balloon catheter comprises two balloon catheters, each of which is carrying an inflatable balloon and is movable through the corresponding push shaft lumen.

In some embodiments, the side openings of both push shafts are facing each other at a non-zero angle.

Certain embodiments of the present invention may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures.

DETAILED DESCRIPTION OF SOME EMBODIMENTS

Figure 1:
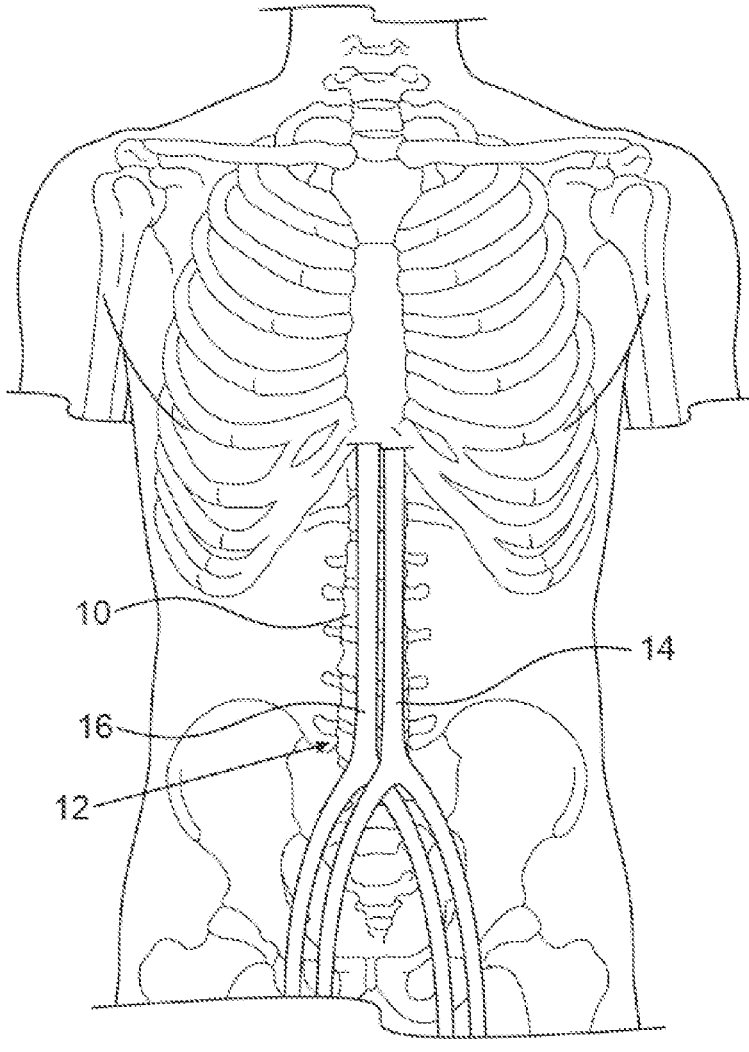
FIG. 1 schematically shows a partial anatomical view of main blood vessels extending along a patient's spine, focused at the abdominal region.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Throughout the figures of the drawings, different superscripts for the same reference numerals are used to denote different embodiments of the same elements. Embodiments of the disclosed devices and systems may include any combination of different embodiments of the same elements. Specifically, any reference to an element without a superscript may refer to any alternative embodiment of the same element denoted with a superscript. In order to avoid undue clutter from having too many reference numbers and lead lines on a particular drawing, some components will be introduced via one or more drawings and not explicitly identified in every subsequent drawing that contains that component.

FIG. 1 shows a schematic view of the abdominal aorta 14 and the inferior vena cava 16, extending vertically along the spine 10 of a patient, and bifurcating generally near the L5 lumbar vertebra. Compression applied to the abdominal aorta, preferably at a section prior to its bifurcation, may assist in arresting blood flow there-through in the case of injury to an organ that may result in internal bleeding. Disclosed herein is a blood vessel compression apparatus 100, configured to apply compressive pressure on the abdominal aorta 14, and optionally on the inferior vena cava 16 as well, at a location corresponding to the level of the L4-L5 vertebrae 12, in order to assure adequate compression of the blood vessels against the spine 10, wherein the L4-L5 vertebrae 12 level may serve as a convenient access level for the apparatus 100.

Figure 2:
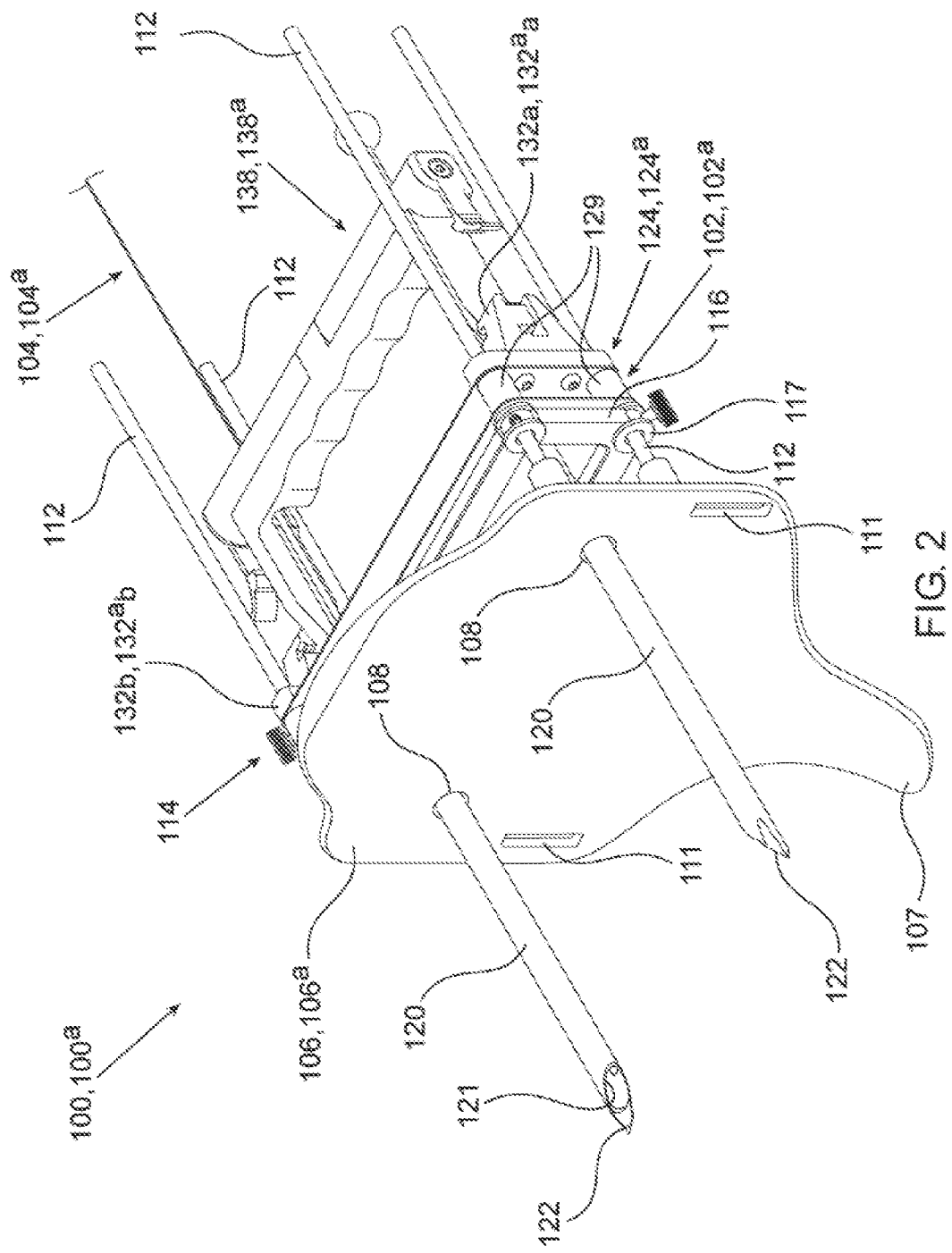
FIG. 2 shows a view in perspective of a blood vessel compression apparatus, according to some embodiments.

FIG. 2 shows a view in perspective of a blood vessel compression apparatus 100, according to some embodiments. Blood vessel compression apparatus 100 comprises an insertion device 102, utilized to provide access to an internal region which is generally distal to the abdominal aorta 14 and/or the inferior vena-cava 16, and a compression assembly 104 delivered through the insertion device 102, and utilized to apply compressive pressure on the abdominal aorta 14 and/or the inferior vena-cava 16, against the spine 10, for example against the L4-L5 vertebrae 12. A specific embodiment of the blood vessel compression apparatus 100$a$ is shown in FIG. 2, including the insertion device 102 and a specific embodiment of the compression assembly 104$^a$.

The term "proximal", as used herein, generally refers to a position, direction, or portion of any device or a component of a device, which is closer to the user of the apparatus 100 situated behind the back of the patient (i.e., behind the site of penetration of the insertion device 102 into the patient).

The term "distal", as used herein, generally refers to a position, direction, or portion of any device or a component of a device, which is further away from the user of the apparatus 100 and closer to the front side of the patient.

The terms "including" and/or "having", as used herein, are defined as comprising (i.e., open language).

The insertion device 102 comprises a base plate 106 dimensioned and shaped for placement over the lumbosacral area of the back of a patient. For example, a front or distal surface of the plate 106 can be curved so as to conformingly fit on the patient's body. In some embodiments, the front or distal surface of the base plate 106 can be textured or coated with materials designed to increase friction when placed over the patient's back, so as to reduce unintentional movement of the insertion device 102 relative to the patient's back once placed thereon.

Figure 6:
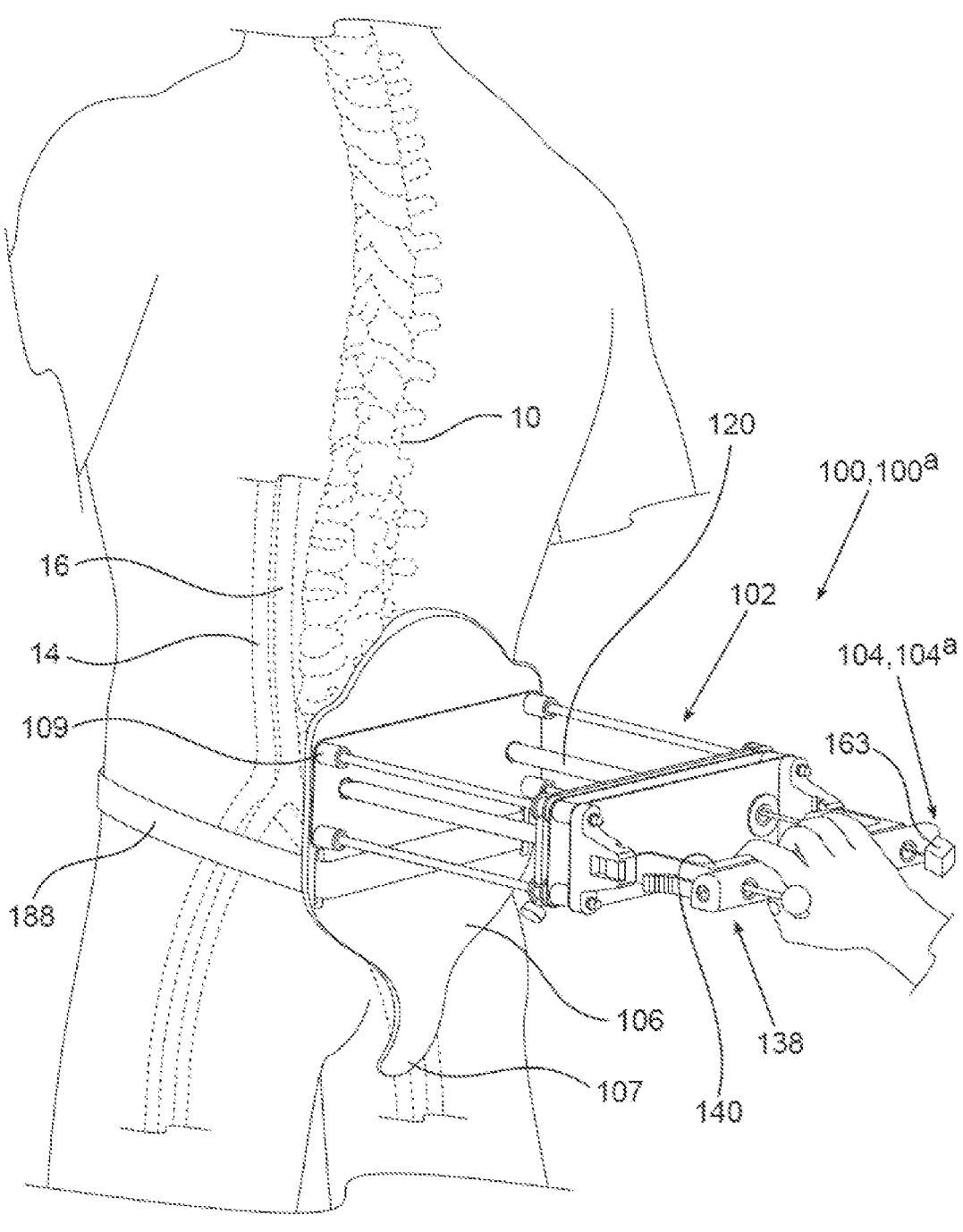
FIG. 6 shows a blood vessel compression apparatus attached to a patient, prior to penetration of the insertion device through the patient's back, according to some embodiments.

In some embodiments, the insertion device 102 may further include adjustable attachment means, such as one or more straps or belts 188 (shown, for example, in FIG. 6). In some embodiments, base plate 106 comprises strap slots 111 through which straps or belts may extend or to which straps or belts can be coupled, so as to allow the insertion device 102 to be secured to the patient's body during the procedure.

The terms coupled, engaged, connected and attached, as used herein, are interchangeable.

In some embodiments, the base plate 106 may comprise a short lower tongue 107, extending downwardly and distally at the lower end of the plate 106. The lower tongue 107 is configured to rest on the sacral area, extending onto the coccyx, straddling the anal area. This may provide further stability to retain the insertion device 102 in position.

The insertion device 102 further comprises one or two introducer shaft 120, axially movable through corresponding one or two base plate openings 108. An embodiment of an insertion device 102$^a$, as illustrated throughout FIGS. 2 to 21, can include a couple of introducer shafts 120 axially movable through two base plate openings 108 of a base plate 106$^a$, while another embodiment of an insertion device 102$^b$, as illustrated throughout FIGS. 22 and 23, can include a single introducer shaft 120 axially movable through a single base plate opening 108 of a base plate 106$^b$.

Each introducer shaft 120 may be formed as a substantially rigid tubular member defining an introducer shaft lumen 121, and comprises a sharp distal end 122. The sharp distal ends 122 of both introducer shafts 120 are adapted to puncture through the patient's back, and preferably advance through the tissues until the sharp distal ends 122 are past the patient's spine 10, and preferably past the abdominal aorta 14 and/or the inferior vena-cava 16. Each sharp distal end 122 defines an opening at the distal end of the introducer shaft lumen 121, through which another shaft, such as a push shaft 156, can extend distally out of the introducer shaft 120.

In some embodiments, the base plate 106 can include one or two extensions (not shown), which can be tubular members extending proximally from the base plate openings 108 and defining channels that are continuous with the base plate openings 108. The number of extensions will match the number of introducer shafts 120. Such extensions may be provided with an axial length selected to support the introducer shafts 120 that may axially move therethrough. In alternative embodiments, the base plate 106 does not necessarily include base support extensions, but may rather have a thickness that is sufficient to provide the desired support to the introducer shafts 120 when passing therethrough.

For embodiments of an insertion device 102a including two introducer shafts 120, both introducer shafts 120 are laterally spaced apart from each other at a distance that is higher than the width of the spine 10 and the main blood vessels, such as the abdominal aorta 14 and the inferior vena cava 16, preferably at a distance that is high enough to ensure that the sharp distal ends 122 do not accidently penetrate or contact the abdominal aorta 14 and the inferior vena cava 16 during advancement into the patient's body. In some embodiments, the lateral distance between both introducer shafts 120 is at least 5 centimeters. In some embodiments, the lateral distance between both introducer shafts 120 is at least 10 centimeters. In some embodiments, the lateral distance between both introducer shafts 120 is at least 15 centimeters. In some embodiments, the lateral distance between both introducer shafts 120 is at least 20 centimeters.

The terms "axial" or "longitudinal", as used herein, are interchangeable and refer to a direction along an axis extending between proximal and distal sides. The term "lateral", as used herein, refers to a direction that is generally perpendicular to the axial direction, extending substantially between the right and left sides of the patient when the insertion device 102 is placed over the patient's back. The term "vertical", as used herein, refers to a direction that is generally perpendicular to the axial direction and to the lateral direction, extending substantially parallel to the height of the patient when the insertion device 102 is placed over the patient's back.

In some embodiments, both introducer shafts 120 of an insertion device 102a are laterally aligned, meaning that both introducer shafts 120, as well as both base plate openings 108, are positioned substantially at the same height measured from a lower end or an upper end of the base plate 106. In other embodiments, both introducer shafts 120 may be vertically offset from each other.

The insertion device 102 comprises means for moving both introducer shafts 120 axially, preferably in a simultaneous manner. In some embodiments, the one or two introducer shafts 120 are affixed at the introducer shaft proximal portions 123 (see FIG. 3) to a push member, such that axial movement of the push member, simultaneously moves both introducer shafts 120 therewith in the case of an insertion device 102a, or moves the single introducer shaft 120 therewith in the case of an insertion device 102b.

In some embodiments, the insertion device 102 further comprises at least one longitudinal guide member affixed to the base plate 106, and extending proximally from the base plate 106 and through a corresponding, at least one guide channel of the push member, such that the push member is axially slidable over the at least one guide member.

In the example embodiment illustrated in FIG. 2, four longitudinal guide members 112 formed as rigid rods are shown, such that each two longitudinal guide members 112 are disposed laterally away from a corresponding introducer shaft 120, above and below the vertical position of the base plate openings 108. The push member includes a matching number of push member guide channels, such as the four push member guide channels aligned with the four longitudinal guide members 112 in the illustrated embodiments.

In some embodiments, the base plate 106 can include guide member support extensions 109 extending proximally from the plate 106, which can be provided in the form of tubular members into which the distal ends of the longitudinal guide members 112 are inserted and/or attached. Such extensions may be provided with an axial length selected to structurally support the guide members 112. In some implementations, as shown, the guide member support extensions 109 are integrally formed or attached to a backplate which is attached to the base plate 106.

Figure 3:
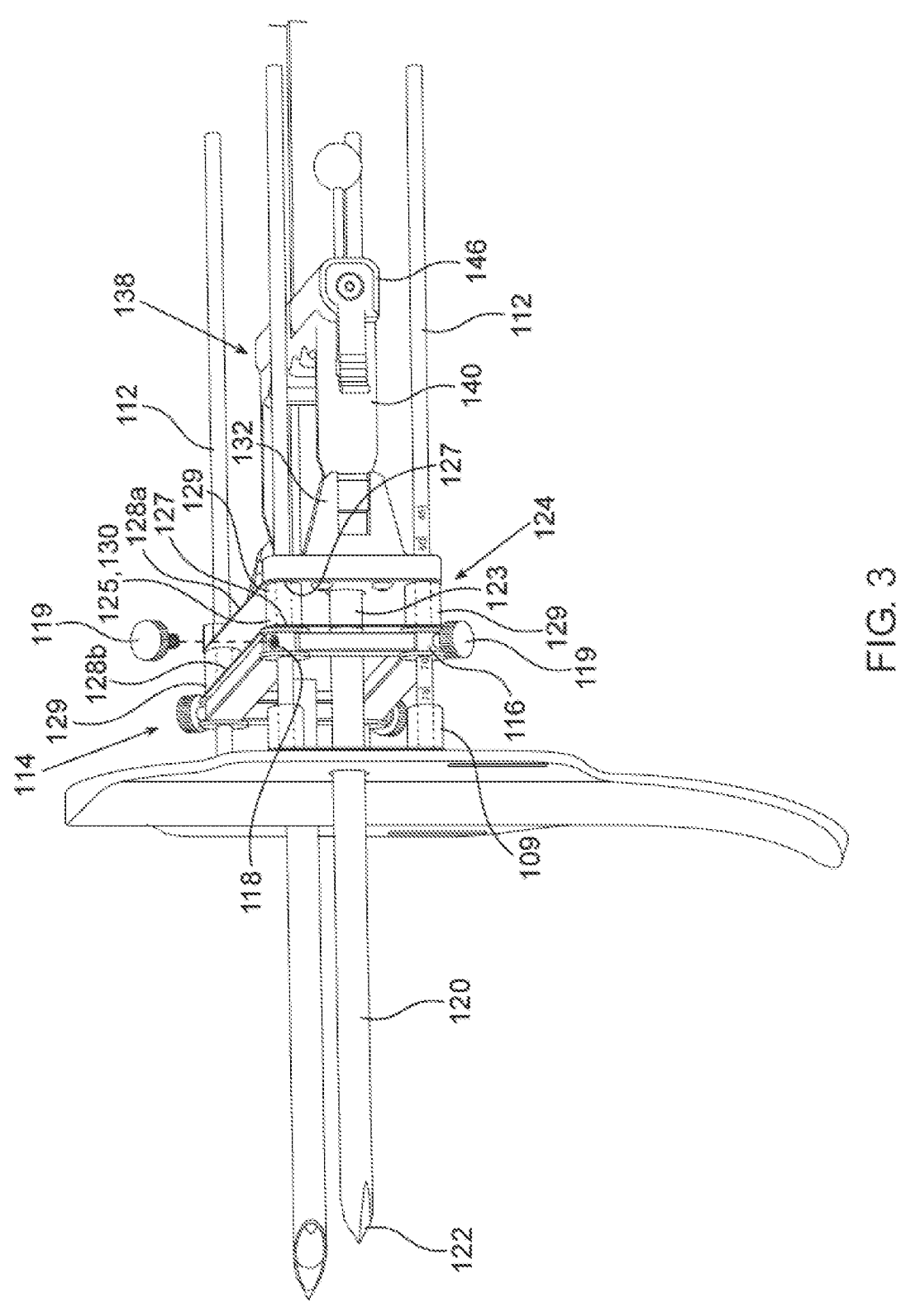
FIG. 3 shows a view in perspective of a blood vessel compression apparatus equipped with a push member comprising two plates and a stopper comprising a slidable frame, according to some embodiments.

FIGS. 2-3 show an embodiment of a push member 124 (or push member 124a in the case of an insertion device 102a), that comprises two push plates 128, such as a first push plate 128a and a second push plate 128b, attached to each other via at least one, and optionally a plurality of, push support extensions 129 disposed therebetween. Four push support extensions 129 are shown at four corners of the push member 124, aligned with the longitudinal guide members 112 and serving as spacers between first and second push plates 128a and 128b. Each push support extension 129 defines a push extension channel 130, and each push plate 128 comprises plate openings 127 aligned with the push extension channels 130, such that each push extension channel 130, combined with both plate openings 127 on either side thereof, together define the corresponding push member guide channel 125 dimensioned to allow a corresponding longitudinal guide member 112 to extend therethrough.

The term "plurality", as used herein, means more than one.

In some embodiments, the push plates 128 are relatively thin plates. The push support extensions 129 are configured to provide additional longitudinal support to the push member 124 slidable over the longitudinal guide members 112. In some embodiments, both push plates 128 have the same thickness. In some embodiments, the thickness of any push plate 128 is not greater than 5 millimeters. In some embodiments, the thickness of any plate 128 is not greater than 1 millimeter. In some embodiments, the length of the push support extensions 129 is at least as great as 1 centimeter. In some embodiments, the length of the push support extensions 129 is at least as great as 2 centimeters.

Figure 4:
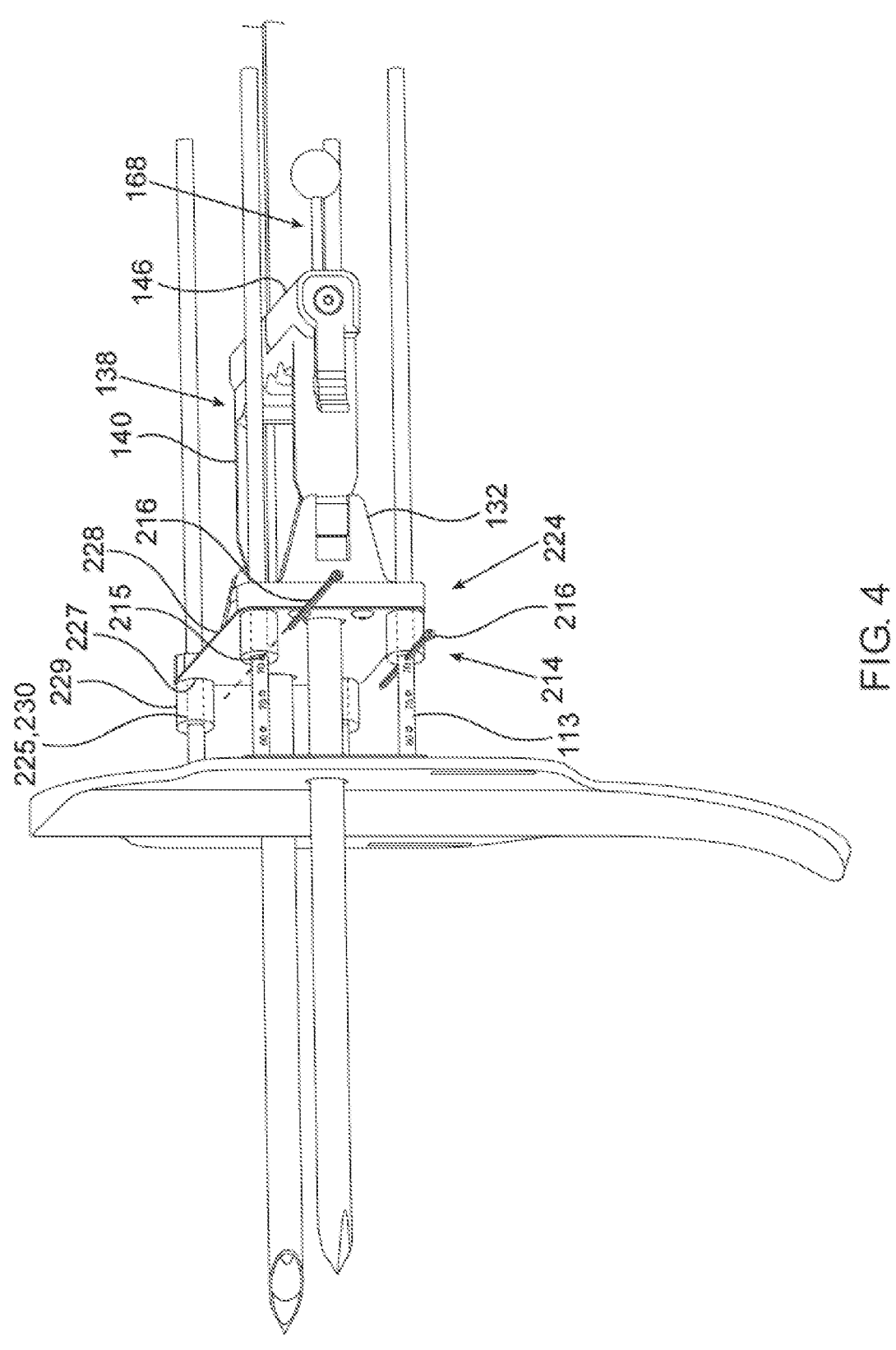
FIG. 4 shows a view in perspective of a blood vessel compression apparatus equipped with a push member comprising a single plates and a stopper comprising a cotter pin, according to some embodiments.

FIG. 4 shows another embodiment of a push member 224 that comprises a single push plate 228, that can be identical to any of the first push plate 128a or second push plate 128b, and push support extensions 229 that can be identical to push support extensions 129, affixed to the push plate 228 and extending axially therefrom. Similarly, each push support extension 229 defines a push extension channel 230 aligned with a corresponding plate opening 227 of the push plate 228, such that each push extension channel 230 and adjacent plate opening 227, together define a corresponding push member guide channel 225. While push support extensions 229 are shown to extend distally from the push plate 228, it is to be understood that push support extensions 229 can alternatively extend distally from the push plate 228.

FIG. 5 shows another embodiment of a push member 324 that comprises a single plate 328 without any additional push support extensions attached thereto and extending therefrom. The push plate 328 may be relatively thicker than thin push plates 128 or 228, such that the plate opening 327 are long enough to provide adequate longitudinal support to push member 324 slidable over the longitudinal guide members 112, without requiring additional support extensions. In some embodiments, the thickness of plate 328 is at least as great as 1 centimeter. In some embodiments, the thickness of plate 328 is at least as great as 2 centimeters.

While four longitudinal guide members 112 are illustrated, in the form of rods or tubes extending through four corners of the push member, it is to be understood that any other number and shapes are contemplated. For example, in alternative embodiments, less or more than four guide members are provided. In some embodiments, two longitudinal guide members, which can be also formed as rods or tubes 112, can extend through opposite sides of the push member, for example at the mid-height level of the push member. In some embodiments, the longitudinal guide members can have a non-circular cross-sectional shape, such as a rectangular cross-section, with height and width that can be equal or different from each other. In some embodiments, two longitudinal guide members can extend through corresponding guide channels at the upper and lower edges of the push member. In some embodiments, a single longitudinal guide member can be provided, for example having a substantially rectangular shape configured to extend through a similarly rectangularly shaped channel following the contour of the outer edges of the push member.

While the plates of the different illustrated embodiments are shown to have generally a rectangular profile across a plane that is orthogonal to the longitudinal direction, it is to be understood that other profiles are contemplated. For example, any of the plates may be shaped as a frame, that can be generally similar in shape to the slidable frame 116 illustrated in FIG. 2. In other embodiments, any of the plates may have an I-shaped profile, for example including two vertically extending portions on its right and left sides, and a narrower lateral portion extending between the vertical portions (embodiments not shown).

It is to be understood that any mention of a push member without a numeral reference throughout the current specification, may refer to any of the push member 124, push member 224, push member 324, as well as other embodiments of the push member.

In some embodiments, the insertion device 102 further comprises at least one stopper attached or attachable to at least one longitudinal guide member 112, and configured to prevent axial advancement of the push member along the at least one longitudinal guide member 112 beyond the stopper, toward the base plate 106.

In some embodiments, the stopper is affixed to the corresponding one or more longitudinal guide member 112. In other embodiments, the stopper is removably attachable to the one or more longitudinal guide member 112, and may transition between a released state, during which it can slide along the longitudinal guide member 112, and a locked state, in which it is secured to the one or more longitudinal guide member 112 at the selected axial position there-along. This option may enable the user to select an axial position of the stopper, thereby defining the maximal advancement of the push member and the corresponding penetration depth of the introducer shafts 120 into the patient's body. Such selection may allow flexibility in adapting the depth of penetration of the introducer shafts 120 according to various parameters, such as the gender of the patient, the body mass or size of the patient, the age of the patient, and the like.

FIGS. 2-3 show an embodiment of stopper 114, that comprises at least one slidable member 116 having a corresponding stopper channel 117 through which the longitudinal guide member 112 extends, such that the slidable member 116 may be axially movable over the corresponding longitudinal guide member 112. In some embodiments, the at least one slidable member 116 further comprises a stopper side opening 118, which extends therethrough up to the corresponding stopper channel 117, oriented perpendicularly to the axial direction of the longitudinal guide member 112. The stopper side opening 118 can be internally threaded, and the stopper 114 can include a compression bolt 119 which can be threaded through the stopper side opening 118 to press lock it against the guide member 112.

In the illustrated embodiment, the slidable member is shown as a slidable frame 116, defining four stopper channels 117 at its four corners, through which the four corresponding longitudinal guide members 112 extend. Four stopper side openings 118 extend at the four corners toward the longitudinal guide members 112, such that when the compression bolts 119 are not pressed against the longitudinal guide members 112, the stopper 114 is in a released state and may be axially movable to a desired position.

In some embodiments, at least one longitudinal guide member 112, to which the stopper is attached or attachable, comprises markings 113 thereon (see, for example, FIG. 4) for assisting a user to associate a selected axial position with a specific characteristic associated therewith. For example, a series of markings can be associates with a patient gender, age, body size and the like.

Once positioned at a desired axial position, the stopper 114 can be secured to the longitudinal guide members 112 by threading the compression bolts 119 through the stopper side openings 118 until they are forcibly pressed against the longitudinal guide members 112. In some embodiments, the stopper 114 can include four compression bolts 119 insertable through four corresponding stopper side openings 118 at all four corners of the slidable member 116. In other embodiments, less than four compression bolts 119 are utilized. For example, a single compression bolt 119 threaded through a corresponding stopper side opening 118 at only one of the corners, can be sufficient, in some implementations, to immovably secure the stopper 114 in position.

In some embodiments, longitudinal guide members 112 can include a series of threaded bores, axially spaced from each other, through which bolt 119 can be threaded, wherein each threaded bore can correspond to a different axial position along which the stopper can be secured.

While a stopper in the form of a substantially rectangular frame 114 is illustrated in FIGS. 2-3, it is to be understood that other shaped are contemplated. For example, the stopper can include an I-shaped profile, with two vertically extending portions on its right and left sides, and a narrower lateral portion extending between the vertical portions (embodiments not shown).

In some embodiments, the stopper comprises another form of at least one slidable element which is not necessarily a frame, For example, a slidable element can be provided in the form of a ring disposed around longitudinal guide members 112, the ring defining a stopper channel that is similar to stopper channel 117, and a side opening that is similar to side opening 118, through which a compressible bolt 119 may be inserted to secure the slidable ring to the longitudinal guide members 112 at a selected axial position. In such embodiments, a plurality of slidable rings may be provided, each ring disposed over a separate different longitudinal guide member 112. Alternatively, a single slidable ring can be provided over a single longitudinal guide member 112, which can be any longitudinal guide members 112 if the insertion device 102 comprises a plurality of longitudinal guide members 112.

FIG. 4 shows another embodiment of a stopper 214 that comprises at least one cotter pin 216 (or any other type of elongated pin), insertable into one or more guide member side opening 215 formed within longitudinal guide members 112. Any longitudinal guide members 112 can include a plurality of guide member side openings 215, axially spaced apart from each other, each corresponding to a different axial position, wherein the cotter pin 216 can be inserted into a selected opening 215 to prevent distal movement of the push member beyond its position. In some embodiments, a plurality of the longitudinal guide members 112 include guide member side openings 215, and more than one elongated pin 216 can be utilized, each insertable into a guide member side opening 215 of a different longitudinal guide members 112. Alternatively, a single elongated pin 216 can be used with a single longitudinal guide member 112, which can be any longitudinal guide members 112 if the insertion device 102 comprises a plurality of longitudinal guide members 112.

In some embodiments, the stopper can be in the form of at least one bolt, for example similar to bolt 119, that can be threaded into a threaded guide member side opening, that can be similar to the openings 215, except for including an inner threading. Any longitudinal guide members 112 can include a plurality of threaded side openings, axially spaced apart from each other, each corresponding to a different axial position, wherein the bolt can be screwed into a selected opening to prevent distal movement of the push member beyond its position. In some embodiments, a plurality of the longitudinal guide members 112 include threaded side openings, and more than one bolt can be utilized, each screwed into a threaded side opening of a different longitudinal guide members 112. Alternatively, a single bolt can be used with a single longitudinal guide member 112, which can be any longitudinal guide members 112 if the insertion device 102 comprises a plurality of longitudinal guide members 112.

In some embodiments, the stopper comprises an extension that can extend radially away from a longitudinal guide member 112, and may be integrally formed therewith. In such embodiments, a user of the insertion device 102 cannot select the axial position of the stopper, but rather the stopper is affixed at a specific axial position. In some embodiments, a plurality of the longitudinal guide members 112 include extensions projecting radially therefrom. Alternatively, a single extension can project from a single longitudinal guide member 112, which can be any longitudinal guide members 112 if the insertion device 102 comprises a plurality of longitudinal guide members 112.

Figures 5A, 5B:
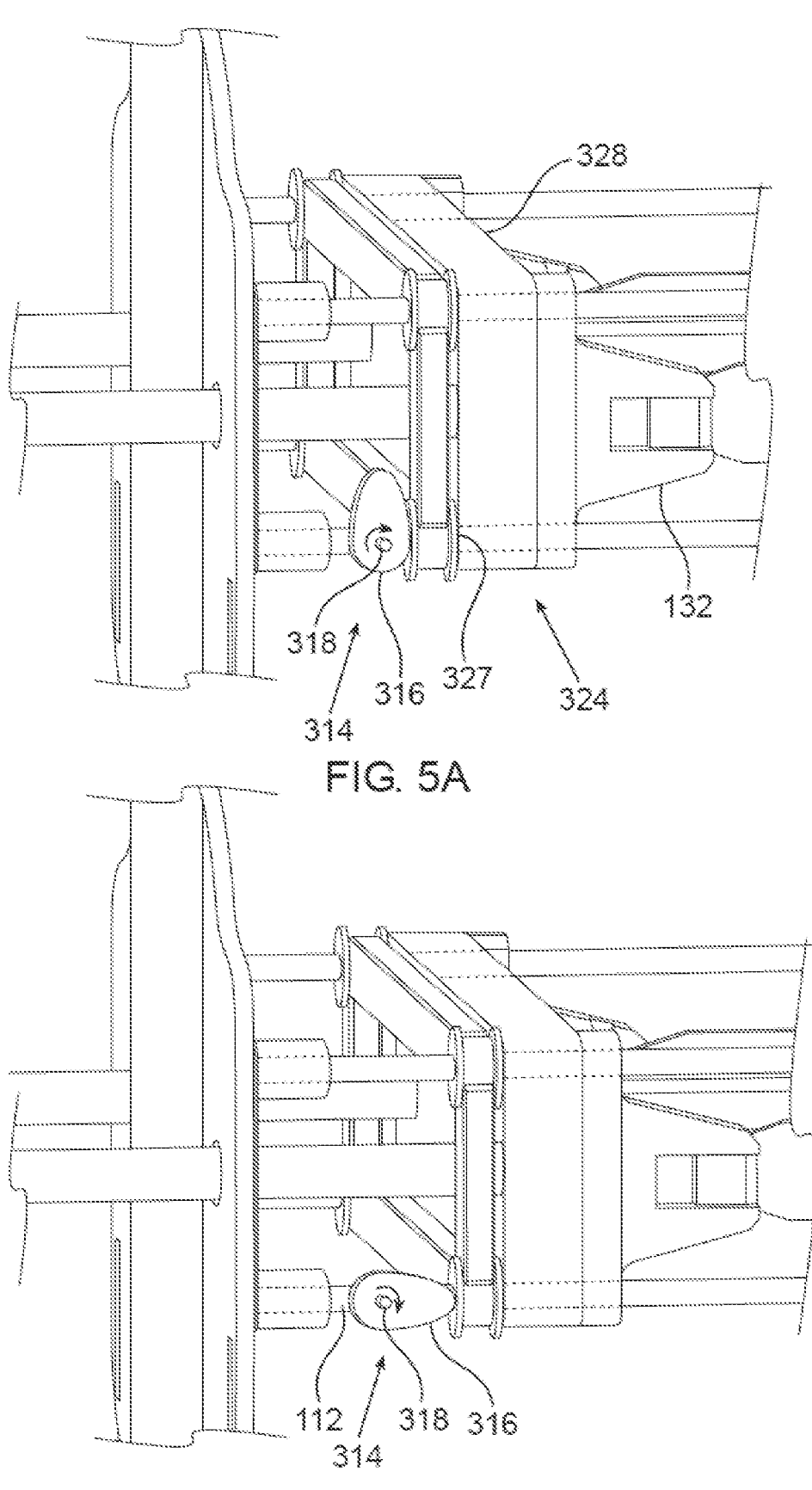
FIGS. 5A-B show two configurations of a stopper comprising a rotatable cam, according to some embodiments.

FIGS. 5A-B show another embodiment of a stopper 314 that comprises at least one rotatable cam 316 hinged to longitudinal guide member 112. The cam can be formed as a lobe having an outer edge following varying distances from the central hinge 318 along the circumference thereof. Depending on the angular orientation of the cam 316, the length between central hinge 318 and the edge of the cam along the axial direction (i.e., parallel to the longitudinal guide member 112) directed proximally (i.e., toward the push member), may vary between a minimal distance (e.g., as shown in FIG. 5A) and a maximal distance (e.g., as shown in FIG. 5B), each corresponding to a different axial stopping position of the push member. In some embodiments, a plurality cams 316 can be hinged to a plurality of longitudinal guide members 112. Alternatively, a single cam 316 can be hinged to a single longitudinal guide member 112 (as in the illustrated example shown in FIGS. 5A-B), which can be any longitudinal guide members 112 if the insertion device 102 comprises a plurality of longitudinal guide members 112.

It is to be understood that any mention of a stopper without a numeral reference throughout the current specification, may refer to any of the stopper 114, stopper 214, stopper 314, as well as other embodiments of the stopper.

The insertion device further comprises a handle assembly 138 attached to the push member, and in some embodiments, releasably attached to the push member. A embodiments of a handle assembly 138a of an insertion device 102a is illustrated throughout FIGS. 2 to 21. In some embodiments, the handle assembly 138 comprises a first stage handle 140 coupled to a second stage handle 146. In some embodiments, the first stage handle 140 is rotatably coupled to the second stage handle 146, such that it may be rotate about a lateral axis of the second stage handle 146. In some embodiments, the first stage handle 140 is releasably coupled to the second stage handle 146. In some embodiments, any of the first stage handle 140 and/or the second stage handle 146 is releasably coupled to the push member.

The term "and/or" is inclusive here, meaning "and" as well as "or". For example, "first stage handle 140 and/or second stage handle 146" encompasses, first stage handle 140, second stage handle 146, and first stage handle 140 with second stage handle 146; and, such "first stage handle 140 and/or second stage handle 146" may include other elements as well.

In some embodiments, the push member comprises at least one bracket, and preferably two brackets 132, such as first bracket 132$^a$a and second bracket 132bb illustrated throughout FIGS. 2 to 21 for an insertion device 102$^a$, wherein any of the first stage handle 140 and/or the second stage handle 146 may be releasably coupled to the brackets 132. In some embodiments, the brackets 132 are attached to, and extend from, a plate of the push member, such as any of plate 128, plate 228, or plate 328. While the brackets 132 in the illustrated embodiments are shown to extend proximally from a rear plate of the push member, it is to be clear than in other embodiments, the brackets can extend in other directions, such as distally from a plate of the push member. Moreover, in some embodiments, the brackets can be attached to the sides of the push member, such as being placed between a first plate 128a and a second plate 128b (embodiments not shown).

It is to be understood that while two brackets 132 separately attached to the push member are illustrated, they may be similarly implemented as a unitary structure attached to the push member, with two extensions on each side extending in the form of the illustrated separate brackets, in which case the term "brackets 132" refers to the two extensions of the unitary structure, and not necessarily separate members as shown.

In some embodiments, each bracket 132 comprises a curved rail 134 (visible, for example, in FIGS. 8-9) extending between its upper and lower ends, wherein the rail 134 is open ended at an end thereof, such as at its upper end or lower end, and optionally may be open ended at both ends thereof.

Figures 8, 9:
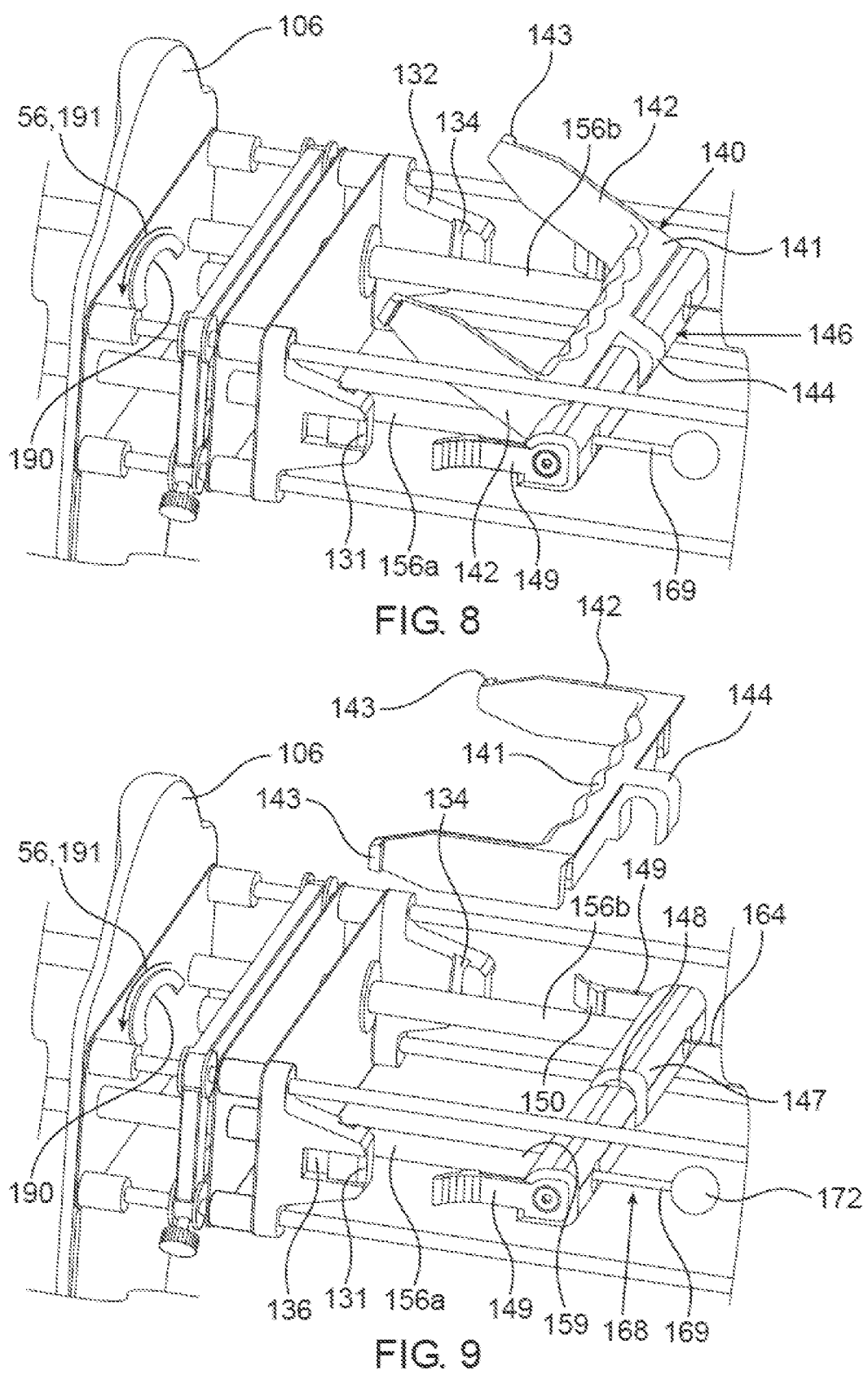
FIG. 8 shows a view in perspective of the handle assembly, wherein the first stage handle is coupled to the second stage handle, but released from brackets extending from the push member, according to some embodiments.
FIG. 9 show a view in perspective of the handle assembly, wherein the first stage handle is disengaged from the second stage handle, according to some embodiments.

The first stage handle 140 can include a first handle main body 141 laterally extending between two first handle side extension 142 (see, for example, FIGS. 8-9). In some embodiments, each first handle side extension 142 comprises a guide projection 143 that may be positioned within a corresponding curved rail 134, and may be slidably movable therein along the path of the curved rail 134. The first handle main body 141 may be sized and shaped for manual holding and pushing and pulling thereof by an operator of the insertion device 102.

The second stage handle 146 can similarly include a second handle main body 147 laterally extending between two resilient locking arms 149. The second handle main body 147 may be similarly sized and shaped for manual holding and pushing and pulling thereof by an operator of the insertion device 102.

FIG. 6 schematically shows a first stage of a method for utilizing blood vessel compression apparatus 100, and more specifically, for utilizing an insertion device 102. This stage can include placement of the insertion device 102 over the back of the patient, and more specifically, placement of the base plate 106 over the lower back of the patient, optionally while the lower tongue 107 rests on the sacral area, extending onto the coccyx, straddling the anal area. Placement of the lower tongue 107 in this position may serve to align the base plate openings 108 at a desired level for penetration of the introducer shafts 120 into the patient's back, for example at the level of the L4-L5 vertebrae 12. The distal ends 122 of the introducer shafts 120 are positioned initially proximal to the distal surface of the base plate 106, such that the distal ends 122 do not protrude out of the base plate openings 108 an do not contact the patient's skin while the insertion device 102 is placed over the lower back.

Figure 7:
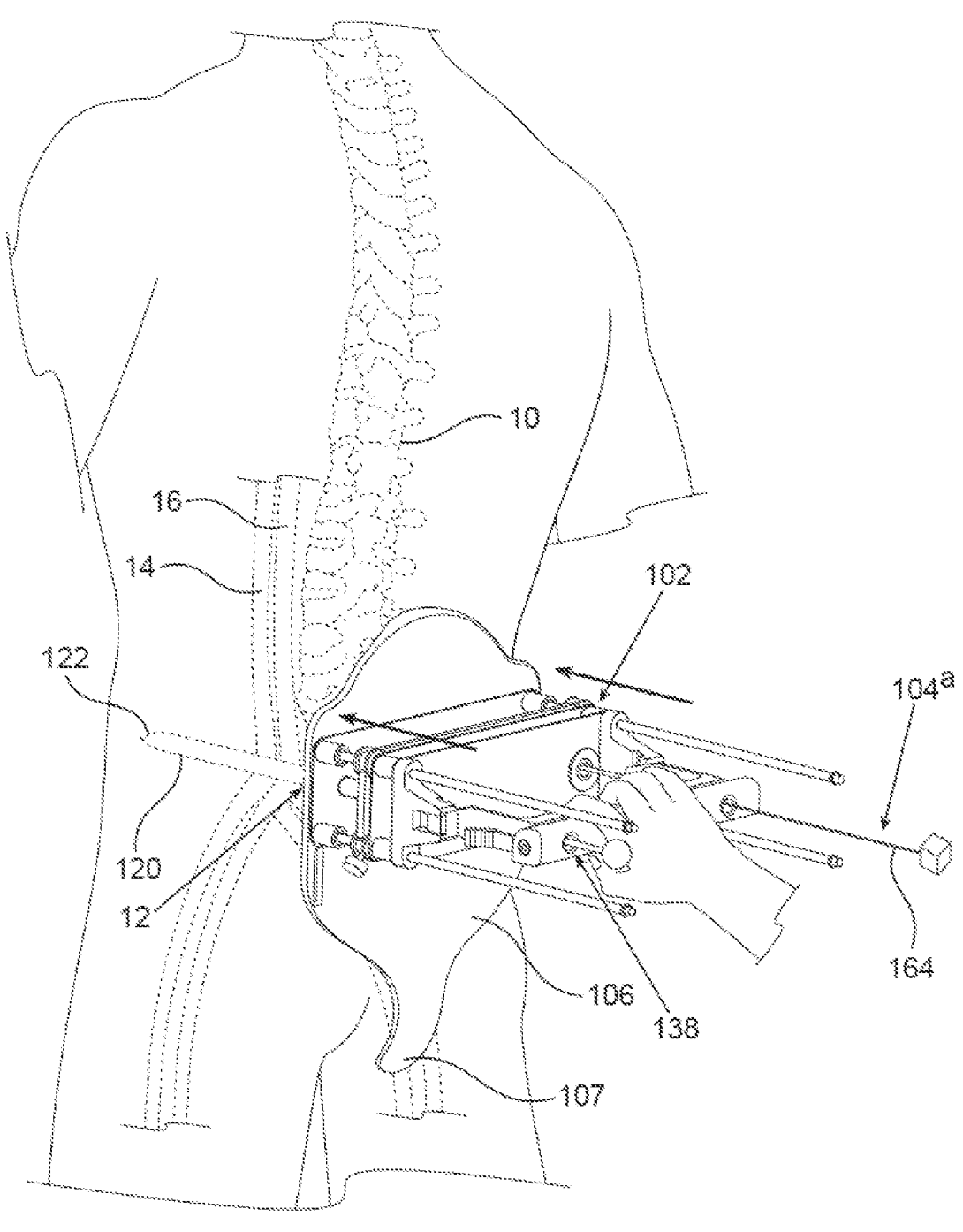
FIG. 7 shows a blood vessel compression apparatus attached to a patient, after penetration of the insertion device through the patient's back, according to some embodiments.

FIG. 7 schematically shows a subsequent stage of a method for utilizing a blood vessel compression apparatus 100, and more specifically, for utilizing an insertion device 102. Once properly placed over the patient's lower back, a user of the insertion device 102 may grab and push the first stage handle 140 and push it in a distal direction. The first stage handle 140 is engaged with the push member at this stage, for example by having its guide projections 143 placed within the curved rails 134 of the brackets 132 of the push member (e.g., of push member 124). Thus, when the first stage handle 140 is pushed distally, the push member (e.g., push member 124), as well as both introducer shafts 120 attached thereto, move distally there-along. The sharp distal ends 122 serve to penetrate through the patient's skin and tissue, such that the introducer shafts 120 are advanced, for example until the push member is stopped by the stopper (e.g., stopper 114).

If the insertion device 102 includes a stopper that may be adjusted, it is assumed that the stopper is secured at a selected axial position prior to pushing the first stage handle 140, for example before or after placement of the base plate 106 over the patient's back. The extent to which the push member is pushed by the user, for example as dictated by the axial position of the stopper, is commensurate with the penetration length of the introducer shafts 120 into the patient's body, preferably such that the sharp distal ends 122 are positioned distal to the spine 10, and optionally distal to the abdominal aorta 14 and/or the inferior vena cava 16.

In some embodiments, the first stage handle 140 is rotatable over the second stage handle 146 such that rotation of the first stage handle 140 slidably moves the guide projections 143 along the arcuate path within the curved rails 134. In some embodiments, the first handle main body 141 includes a clip 144 engaged with a corresponding coupling recess 148 of the second handle main body 147 (see FIGS. 8-9). In other embodiments, the second handle main body 147 may be uniformly shaped, without a recess, such that the clip 144 is coupled to the second handle main body 147, for example at a portion of its outer surface.

While a single clip 144 is shown extending from the middle of the first handle main body 141, and engaged with a single corresponding coupling recess 148 at the middle of the second handle main body 147, it is to be understood that other configurations of more than one clip 144 and one coupling recess 148 are contemplated, and wherein the clip 144 and the coupling recess 148 can be positioned at other positions along the length of the first handle main body 141 and the second handle main body 147, respectively.

In some embodiments, the clip 144 is C-shaped or U-shaped, thereby allowing the first stage handle 140 to be released from the second stage handle 146. In alternative embodiments, the clip is ring-shaped such that it may allow rotational engagement over the corresponding coupling recess 148, without allowing the first stage handle 140 to disengage from the second stage handle 146 (ring-shaped clip embodiment not shown).

FIG. 8 schematically shows a subsequent stage of a method for utilizing a blood vessel compression apparatus 100, and more specifically, for utilizing an insertion device 102. Once the introducer shafts 120 have been fully extended into the patient's body, the first stage handle 140 can be rotated by the user about the lateral axis of the second stage handle 146, during which the guide projections 143 follow the rotational movement until they are released from the corresponding curved rails 134 through their open ends.

FIG. 9 schematically shows an optional subsequent stage of a method for utilizing a blood vessel compression apparatus 100, and more specifically, for utilizing an insertion device 102. If the first stage handle 140 is releasably coupled to the second stage handle 146, for example via a C-shaped or a U-shaped clip 144, it may be pulled away from the second stage handle 146 once the guide projections 143 are released from the rails 134, as shown. In alternative embodiments, wherein the first stage handle 140 is not releasable from the second stage handle 146, it may remain coupled thereto in a state in which the first handle side extensions 142 are not oriented toward the push member, so as to avoid interference with distal movement of the second stage handle 146 in the following stage of the method of utilization.

The insertion device 102 further one or two push shafts 156, axially movable through the introducer shaft lumens 121. An insertion device 102$^a$, as illustrated throughout FIGS. 2 to 21, may include two push shafts 156$^a$, while an insertion device 102$^b$ of the type illustrated in FIG. 22 will include a single push shaft 156$^b$. At least one of the push shaft 156, and in some embodiments, both push shafts 156$a$ and 156$b$, may be formed as a substantially rigid tubular member defining an push shaft lumen 157. In some embodiments, an insertion device 102$a$ will include two non-identical push shafts 156, wherein one of the push shafts 156 is formed as a tubular member defining a lumen 157, while the other push shaft 156 may be formed either as a tubular member or as a rod member that does not necessarily define an internal lumen.

Each push shaft 156 comprises an atraumatic distal end 158. The atraumatic distal ends 158 of both push shafts 156 may be shaped as blunt portions that can be pressed against internal tissues, for example to push such tissues without puncturing, cutting, or otherwise damaging the tissues.

In some embodiments, the push shaft lumen 157 terminates proximal to the distal end 158, such that the distal end 158 may be shaped with full matter that does not necessarily define an axially oriented opening.

In some embodiments, at least one push shaft 156 comprises a side opening 160, proximal to the atraumatic distal end 158 and oriented substantially orthogonally to the axis of the push shaft lumen 157. In some embodiments, both push shafts 156 of an insertion device 102a comprise side openings 160. In some embodiments, the push shafts 156 comprise a first push shaft 156a provided with a first side opening 160a, and a second push shaft 156b provided with a second side opening 160b. In some embodiments, the side opening 160 of any push shaft 156 extends distally up to the distal end 158.

The one or two push shafts 156 are affixed to the second stage handle 146, for example at their proximal portions 159, such that axial movement of the second stage handle 146 displaces the one or two push shafts 156 therewith. In some embodiments, the one or two push shafts 156 are open ended at their proximal ends, allowing other components to be inserted therefrom into their respective lumens 157. In some embodiments, proximal ends of the one or two push shafts 156 are attached to a portion of the second stage handle 146, wherein the second stage handle 146 defines axial channels which are continuous with the push shaft lumens 157 and are open-ended at the rear/proximal end of the second stage handle 146.

In some embodiments, push shaft proximal portions 159 extend through channels of the second stage handle 146 but terminate distal to the proximal end of the second stage handle 146, wherein the channels are open-ended to exposed rear openings which are continuous with the push shaft lumens 157. In some embodiments, portions of the push shafts 156 extend through channels of the second stage handle 146, and are affixed thereto, while the push shaft proximal portions 159 further extend from the rear of the second stage handle 146 and terminate proximally thereto.

When the first stage handle 140 is coupled to the second stage handle 146, and the first handle side extensions 142 are engaged with the brackets 132, the one or two push shafts 156 do not protrude distally from the introducer shafts 120. That is to say, the atraumatic distal ends 158 are hidden within the introducer shaft lumens 121, proximal to the sharp distal ends 122. Thus, when the entire handle assembly 138 is pushed distally, as shown for example in FIG. 7, while both the first stage handle 140 and the second stage handle 146 are attached to each other and are aligned with each other, both the introducer shaft 120 and the push shafts 156 extending through their lumens 121 translate axially in unison. In other words, the first stage handle 140 prevents the second stage handle 146 from moving distally toward the push member, relative to the first stage handle 140, and thus prevents the one or two push shafts 156 from extending distally out of the introducer shafts 120, even when the introducer shafts 120 penetrate into the patient and are advanced distally by the push member.

When the first stage handle 140 is disengaged from the brackets 132 of the push member, either by being merely rotated about a lateral axis as shown in FIG. 8, or by being further decoupled from the second stage handle 146 as well, as shown in FIG. 9, the second stage handle 146 is free to move distally toward the push member, until it is engaged therewith.

In some embodiments, the locking arms 149 are configured to engage with the brackets 132. In some embodiments, the second stage handle 146 is releasably coupled to the brackets 132 via the locking arms 149. In some embodiments, each bracket 132 further comprises a locking socket 136 on the side opposite to that of the curved rail 134, and each locking arm 149 comprises a locking arm projection 150 configured to lock into the locking socket 136. The bracket 132 can optionally include an axial recess 135 extending from its proximal end to the locking socket 136.

Figure 10A:
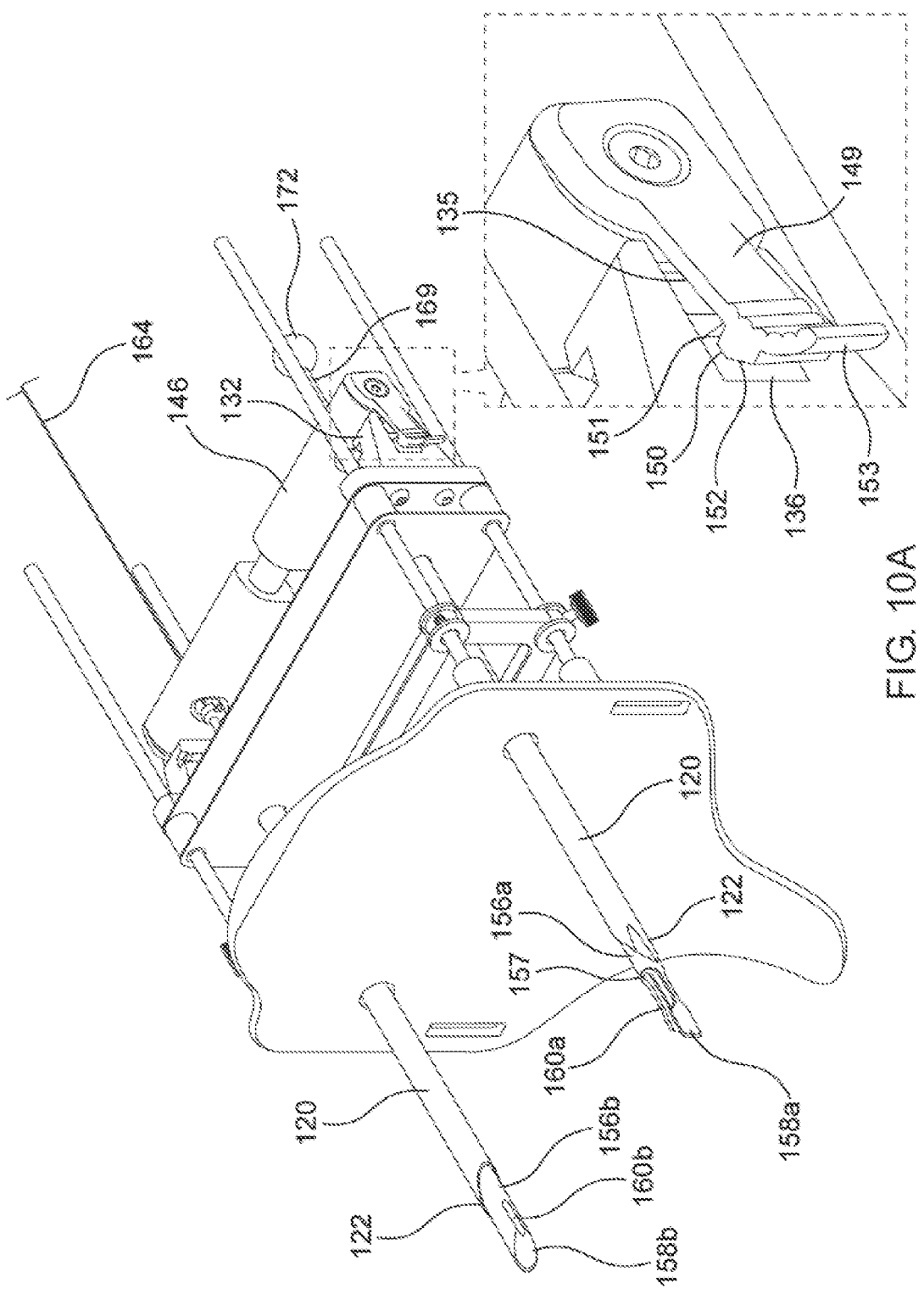
FIGS. 10A-B show steps of coupling the second stage handle to the brackets extending from the push member, according to some embodiments.
Figure 10B:
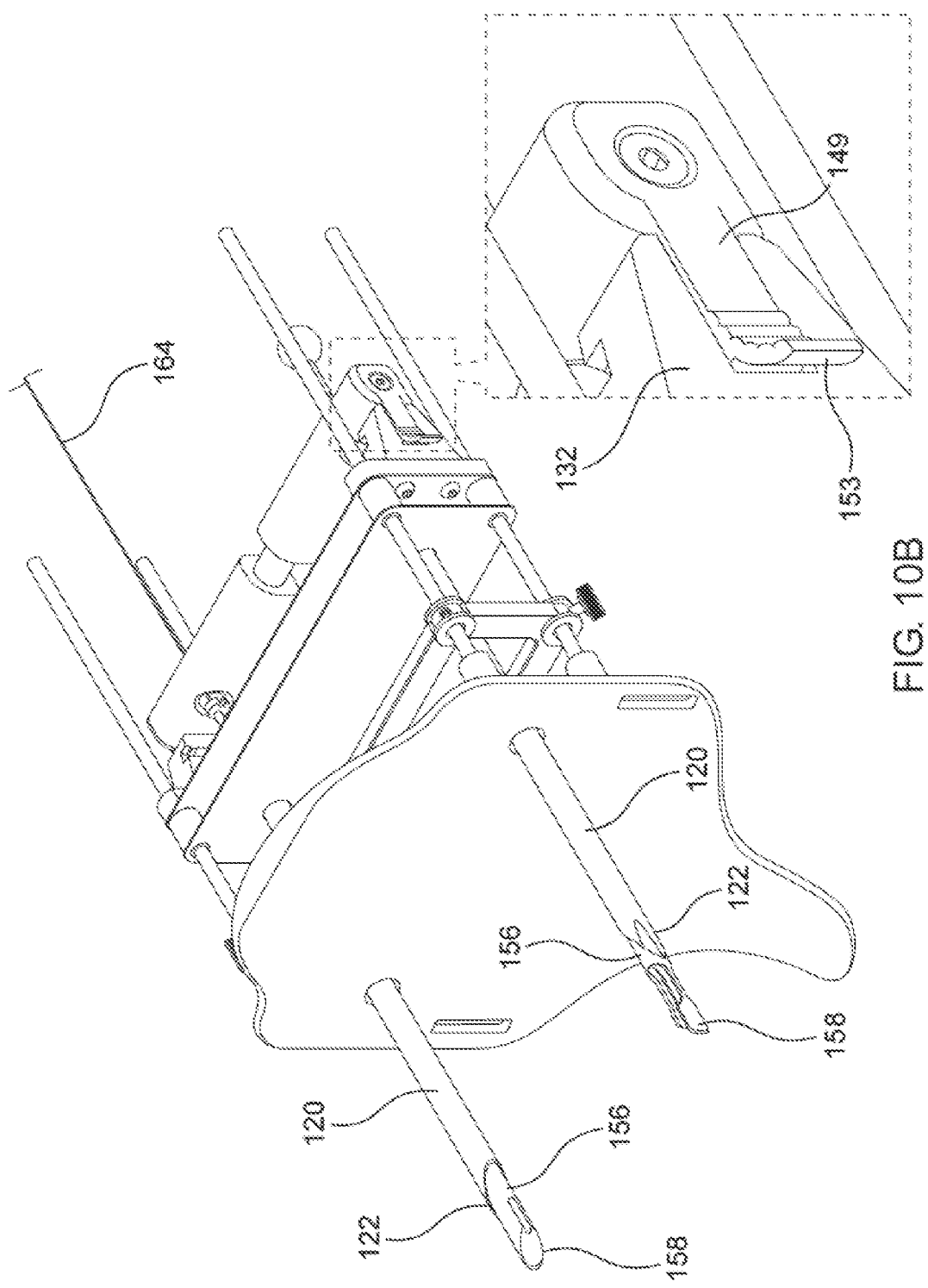

FIGS. 10A-B schematically show an optional subsequent stage of a method for utilizing a blood vessel compression apparatus 100, and more specifically, for utilizing an insertion device 102. When the second stage handle 146 is pushed distally toward the push member, the locking arms 149 can slide over the corresponding brackets 132, as shown in FIG. 10A, until the locking arm projections 150 are snapped into the corresponding locking sockets 136, as shown in FIG. 8B. In some embodiments, each locking arm projection 150 comprises an distally oriented angled surface 152 and a proximal stop portion 151.

The locking arm 149 is biased (e.g., resiliently or spring-biased) inward, toward the bracket 132 (or toward each other when not engaged with the brackets). The angled surface 152 can allow the locking arm 149 to deflect sideways when push distally and engaging the bracket 132. The bracket can also include a similar proximally oriented angled portion 131 (for example, in the form of a chamfered proximal end as illustrated in FIGS. 8-9) to further facilitate this sideways deflection. The projection 150 then slides distally over the bracket, optionally along recess 135, until the projection is snapped inward into the locking socket 136, such that the stop portion 151 prevents spontaneous disengagement or proximal movement of the locking arm 149 away from the bracket 132.

As the second stage handle 146 is pushed distally into locking engagement with the push member, and more specifically, with its brackets 132, the one or two push shafts 156 are pushed there-along from a retained position, wherein their atraumatic distal ends 158 are retained within the introducer shaft lumens 121, proximal to the sharp distal ends 122, to a pushed position, wherein the push shafts 156 extend beyond the introducer shafts, such that their atraumatic distal ends 158 protrude distally from the sharp distal ends 122, and the side openings 160 are exposed from the introducer shafts 120 as well. The distance by which the push shafts 156 translate axially between the retained and pushed positions, is proportional to the length of the first handle side extensions 142.

The couple of push shafts 156 of an insertion device 102$^a$ are preferably configured to push the peritoneum layer (not shown) away from the abdominal aorta 14 and/or the inferior vena cava 16, for forming and maintaining a working space into which components of the compression assembly 104 can extend to a position that is distal to these blood vessels, after which such components can be utilized for applying compressive force to compress such blood vessels, for example against the spine 10, so as to block blood flow therethrough. In the absence of such push members creating this working space, the peritoneum layer can be pressed against, or otherwise located in close proximity to, the abdominal aorta 14 and/or the inferior vena cava 16, in a manner that will interfere with, and potentially completely prevent, extension of any components of the compression assembly 104, or components of other devices that can be used in combination with the insertion device 102, distally to these blood vessels.

In some embodiments, each locking arm 149 further comprises a release tab 153, that can project away from the locking arm projection 150 and shaped to allow the user to push it laterally away from the bracket 132 until the locking arm projection 150 is released from the locking socket 136, thus releasing the second stage handle 146, for example at the end of a procedure or during assemblage of the device.

FIGS. 2 to 14 show embodiments of a blood vessel compression apparatus 100$^a$ comprising an insertion device 102$^a$ and compression assembly 104$^a$. In some embodiments, compression assembly 104$^a$ comprises a wire 164 extending at least partially through the second push shaft lumen 157$b$, and a wire retrieval assembly 168 extending at least partially through the first push shaft lumen 157$a$. The wire retrieval assembly 168 can include a snare loop 170 that may transition between a compressed state and an expanded state. In some embodiments, the wire retrieval assembly 168 further comprises a longitudinal portion 169 extending proximally from the snare loop 170, and movable axially within the first push shaft lumen 157$a$.

In some embodiments, the longitudinal portion 169 is configured to extend proximally out of the first push shaft 156$a$, and include a retrieval proximal stopping portion 172 disposed proximal to the second stage handle 146, and sized to be larger than the first push shaft lumen 157$a$ and/or a channel or proximal opening of the second stage handle 146 aligned therewith. While a retrieval proximal stopping portion 172 in the form of an enlarged bead or ball-shaped member is shown, it is to be understood that other shapes are contemplated.

During insertion of the introducer shafts 120 and pushing the push shafts 156 as demonstrated throughout FIGS. 6-10B, the snare loop 170 at the distal end of the wire retrieval assembly 168 is retained in a compressed state within the first push shaft lumen 157$a$, proximal to the first side opening 160$a$, and the retrieval proximal stopping portion 172 is distanced proximally away from the second stage handle 146.

Wire 164 comprises a wire distal end 165, which is retained within the second push shaft lumen 157$b$, proximal to the second side opening 160$b$, during insertion of the introducer shafts 120 and pushing the push shafts 156 as demonstrated throughout FIGS. 6-10B. In some embodiments, at least a portion of the wire 164 may extend proximally out of the second push shaft 156$b$. In some embodiments, the wire 164 can further include a wire proximal stopping portion 163 disposed proximal to the second stage handle 146, and having a size larger than that of the second push shaft lumen 157$b$ and/or a channel or proximal opening of the second stage handle 146 aligned therewith. While a wire proximal stopping portion 163 in the form of an enlarged bead or ball-shaped member is shown, it is to be understood that other shapes are contemplated.

Figure 11:
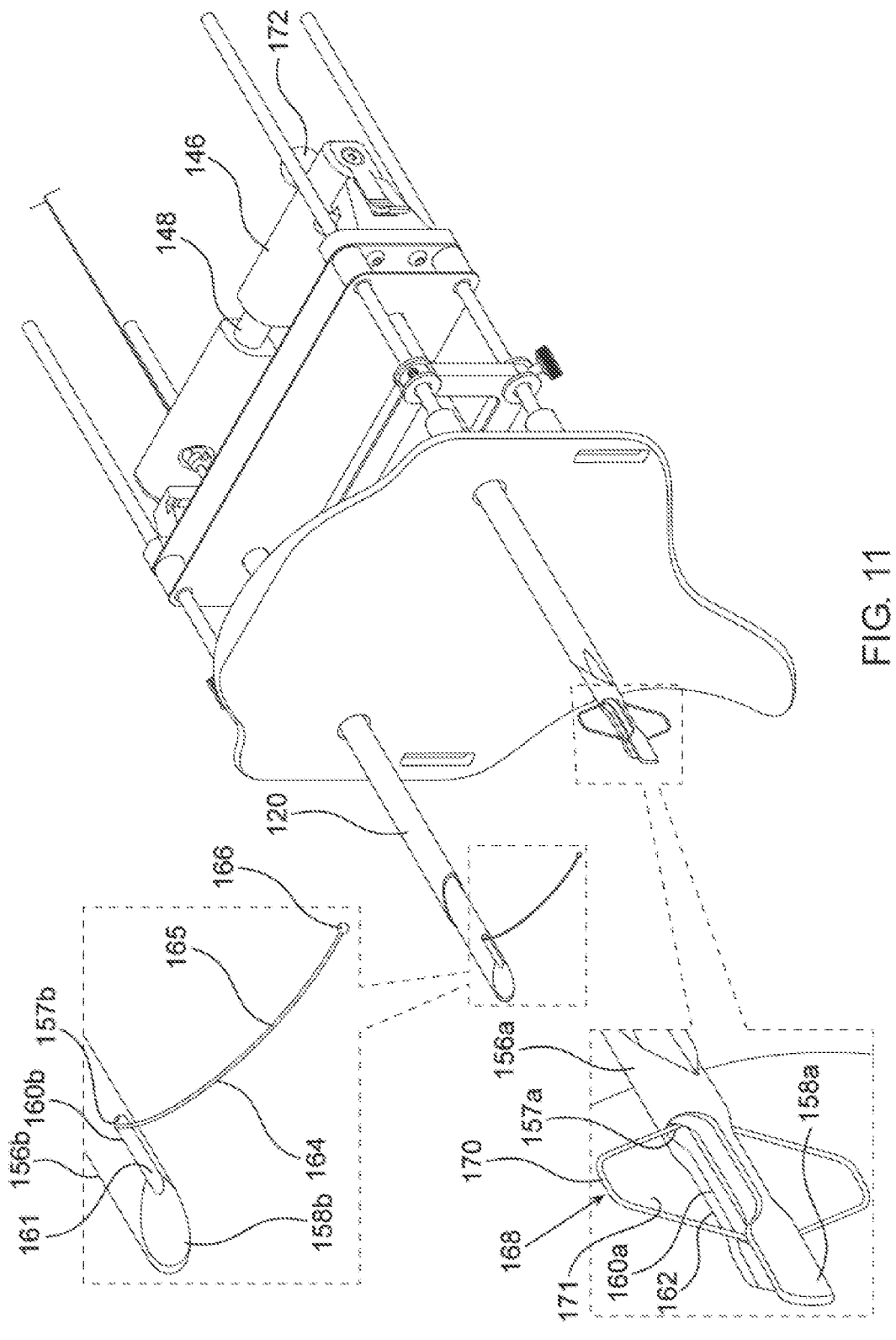
FIG. 11 show a view in perspective of a blood vessel compression apparatus, with an expanded snare loop and a wire partially extending toward the snare loop.
Figures 12A, 12B:
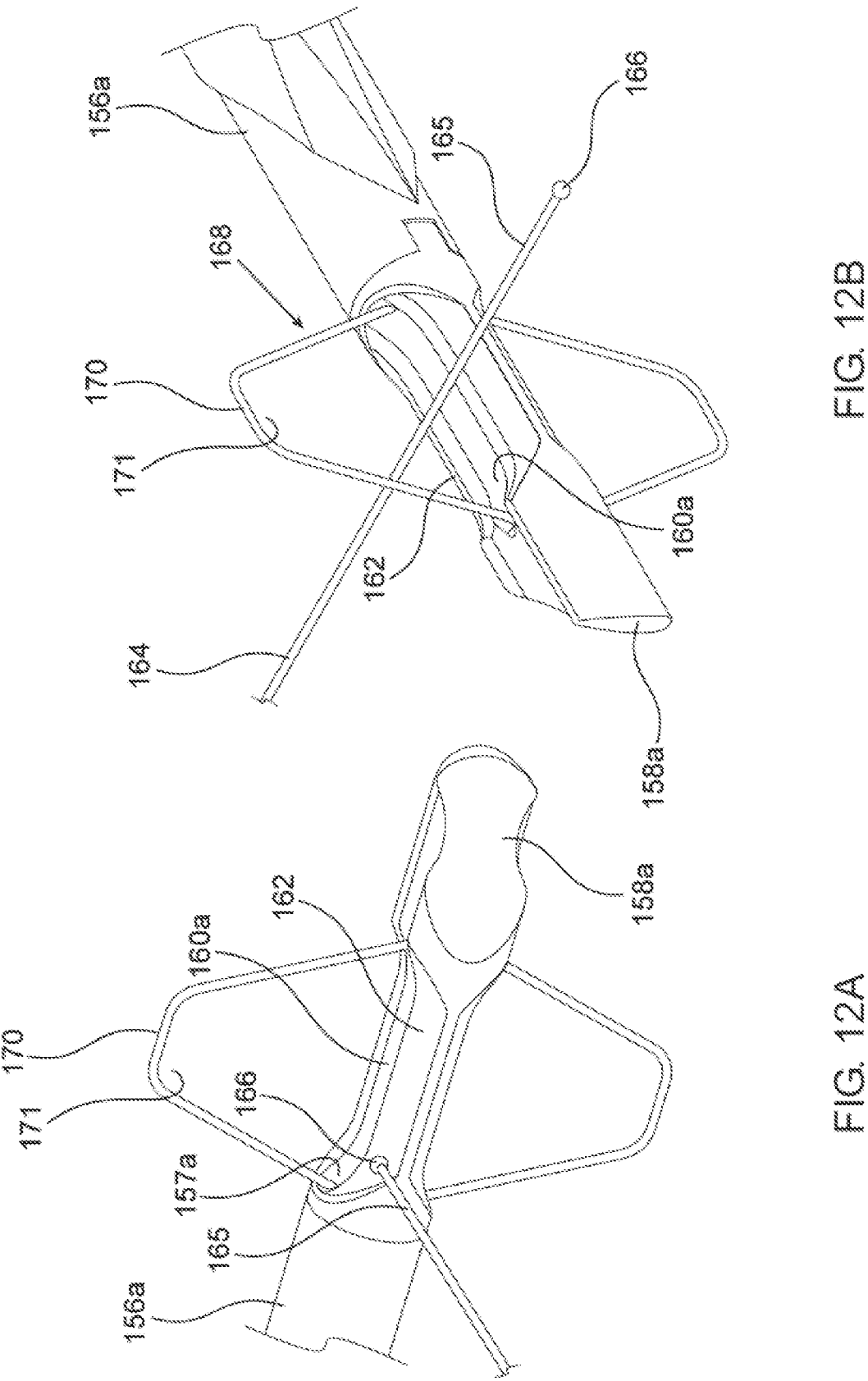
FIGS. 12A-D show consecutive stages of extending the wire through the snare loop, capturing it by the snare loop and pulling through the opposite push shaft lumen, according to some embodiments.
Figures 12C, 12D:
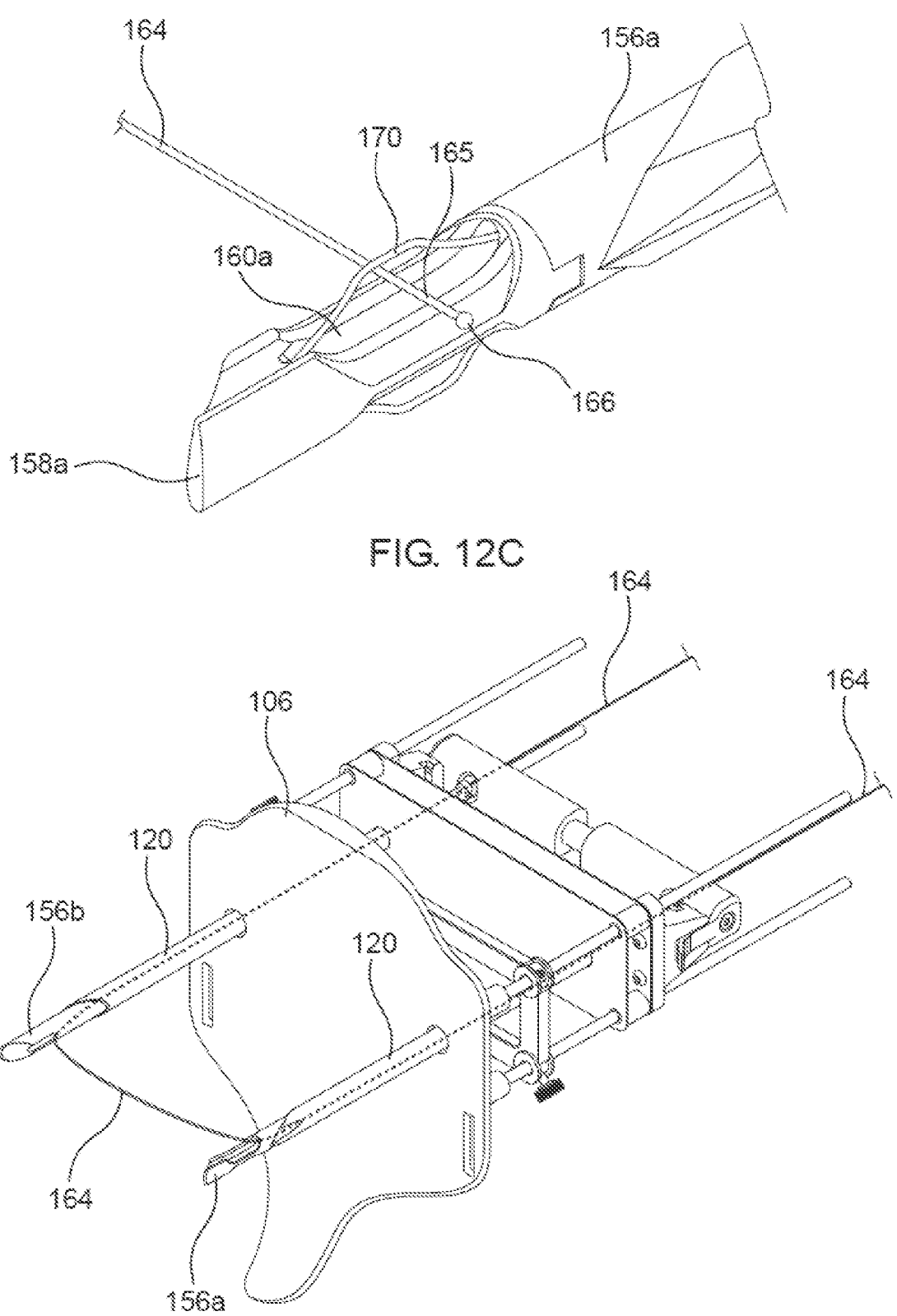

FIGS. 11-12 schematically show subsequent stages of a method for utilizing a blood vessel compression apparatus 100$^a$. Once the push shafts 156 have been advanced distally to provide the desired working space, the wire retrieval assembly 168 can be pushed distally, until the snare loop 170 is exposed through the first side opening 160$a$ and assume an expanded state, defining a loop space 171. In some embodiments, the wire retrieval assembly 168 is advanced until the retrieval proximal stopping portion 172 is stopped, for example by the second stage handle 146. The extent of advancement is proportional to the distance of the retrieval proximal stopping portion 172 from the second stage handle 146 in such cases.

In some embodiments, the first side opening 160$a$ is facing upward or downward with respect to the longitudinal axis of the first push shaft 156$a$, allowing the snare loop 170 to expand so as to define a vertically oriented loop space 171. In some embodiments, the first side opening 160$a$ comprises two opposing openings on both upper and lower sides of the first push shaft 156$a$, allowing the snare loop 170 to expand through both sides of the push shaft 156$a$ through these openings, as shown.

In some embodiments, the snare loop 170 can be made of shape-memory materials, such as, but not limited to, nickel titanium alloy (e.g., Nitinol). When constructed of a shape-memory material, the snare loop 170 can be pre-shaped to self-expand through the first side opening 160$a$ once it is no longer constrained by the inner walls of the first push shaft 156. Alternatively or additionally, the snare loop 170 can assume its expanded configuration when pressed against a distal wall or edge of the first push shaft 156$a$, while the longitudinal portion 169 is further pushed to approximate the snare loop's proximal and distal ends to each other, allowing it to foreshorten axially and expand vertically. In such embodiments, the loop 170 can be formed of other flexible materials, which are not necessarily shape-memory materials, and in some embodiments may be made of interjoined sections with bendable joints or regions. While a hexagonal snare loop 170 is illustrated in FIG. 11, it is to be understood that this is by way of illustration and not limitation, and that other shapes are contemplates, such as elliptic, circular, rectangular, diamond-shaped, and the like.

In some embodiments, the second side opening 160$b$ is oriented laterally, facing the first push shaft 156$a$. Preferably, the second side opening 160$b$ may be laterally aligned with the first side opening 160$a$. The wire 164 can be pushed distally until it reaches the region of the second side opening 160$b$, at which point it may exit through the second side opening 160$b$ and further extend laterally across the working space, toward the first push shaft 156$a$, and more specifically, toward the snare loop 170 in its expanded state.

In some embodiments, the wire 164 can be made of shape-memory materials, such as, but not limited to, nickel titanium alloy (e.g., Nitinol). When constructed of a shape-memory material, the wire 164 can be pre-shaped to bend sideways and strive to exit through the second side opening 160$b$. Additionally or alternatively, the second push shaft lumen 157$b$ can terminate with a deflecting edge 161 at the level of the second side opening 160$b$, such as proximate to its distal end, which can be in the form of an angled surface configured to deflect the wire 164 sideways, through the second side opening 160$b$.

The wire 164 can be further pushed to advance its distal end 165 toward the snare loop 170, until it is passed through the loop space 171. In some embodiments, the wire distal end 165 comprises a rounded or angled portion, such as a round bead 166 shown in the illustrated embodiment, and the edge 162 of the first side opening 160$a$, at least along the portion configured to be contacted by the wire distal end 165, is rounded or chamfered, so as to direct the wire distal end 165 toward and into the loop space 171, as shown in FIG. 12.

In some embodiments, the wire 164 is advanced until the wire proximal stopping portion 163 is stopped, for example by the second stage handle 146. The extent of advancement is proportional to the distance of the wire proximal stopping portion 163 from the second stage handle 146 in such cases. In some embodiments, the wire 164 does not necessarily include a wire proximal stopping portion, but may be wound around a drum proximal to the second stage handle 146 (embodiments not shown).

Figures 13A, 13B:
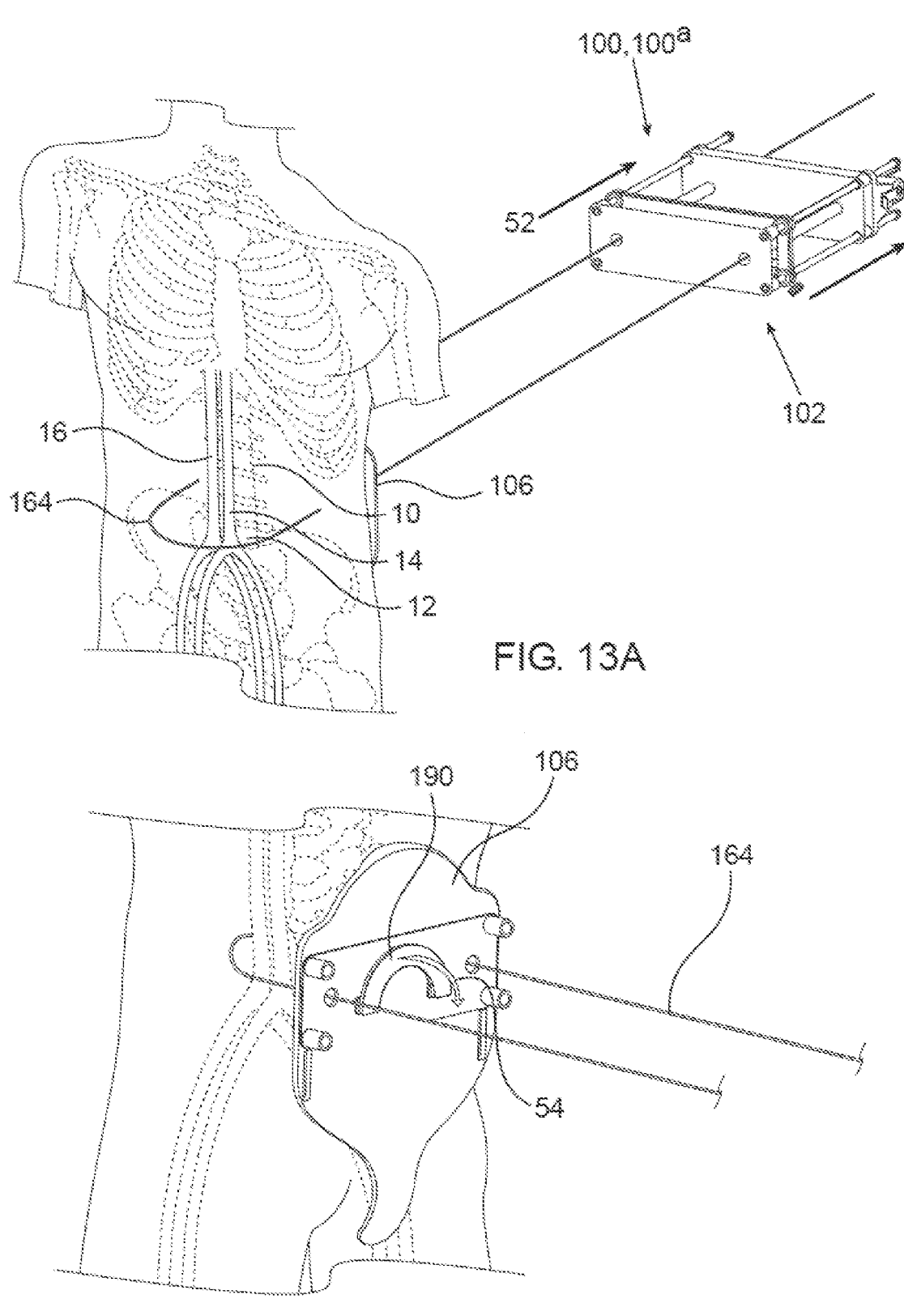
FIGS. 13A-C show consecutive stages of decoupling and removing components of the blood vessel compression apparatus, and rotating the base plate to interwind exposed strands of the wire, according to some embodiments.
Figure 13C:
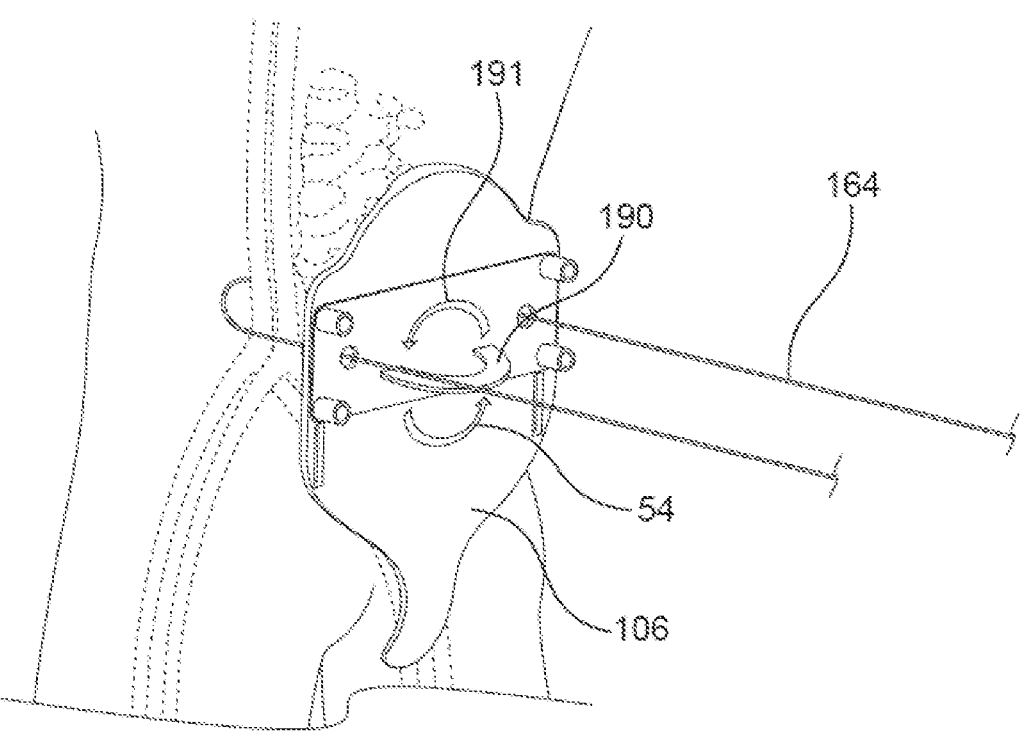

FIGS. 13A-C schematically show steps of a subsequent stage of a method for utilizing a blood vessel compression apparatus 100$^a$. Once the wire distal end 165 extends past the loop space 171, the wire retrieval assembly 168 can be pulled proximally in specific embodiments, for example by pulling on the retrieval proximal stopping portion 172 away from the second stage handle 146. This in turn pulls the snare loop 170 back into the first push shaft lumen 157a and causes it to contract and be tightened over the portion of the wire 164 extending therethrough, such that further pulling the compressed wire retrieval assembly 168, serves to proximally retract the wire 164 therewith through the first push shaft lumen 157a.

In some embodiments, as further shown in FIG. 13A, at least some portions of the blood vessel compression apparatus 100ᵃ, such as components of the insertion device 102ᵃ, can be pulled away (in proximally oriented direction 52) and removed, leaving the strands of wire 164 extending from the patient's back mostly exposed. FIG. 13A shows all components of the insertion device 102a excluding the plate 106a pulled away. Leaving both strands of wire 164 extending proximally through base plate opening 108 exposed.

In some embodiments, the base plate 106a can be manually rotated by a user of the blood vessel compression apparatus 100ᵃ so as to helically intertwine and/or twist both strands of the wire 164, extending proximally from both base plate openings 108, over each other, thereby locking the wire in position. In some embodiments, as shown in FIGS. 8-9 and FIG. 13B, the base plate 106a further comprises a rotating handle 190, which can be grabbed by a user of the blood vessel compression apparatus 100ᵃ to manually rotate the base plate 106ᵃ. An indicator arrow 191 can be printed on the backside of the base plate 106a (i.e., the side facing away from the patient), to indicate a recommended direction of rotation, which can be either clockwise or counterclockwise.

In some embodiments, the rotating handle 190 is a foldable handle, that can be, for example, hinged to the base plate 106ᵃ, and may transition between a folded position, as shown in FIGS. 8-9, during which it is substantially parallel to the base plate 106a in order to prevent interference with other components of the insertion device 102ᵃ during the previous stages as described above, and an extended (or unfolded) position, by pivoting over its hinges downward in direction 54 shown in FIG. 13B. Once assuming its extended position, as shown in FIG. 13C, the handle can be rotated in rotational direction 56 (according to arrow 191, for example), thereby facilitating rotational movement of the whole base plate 106a therewith.

Figure 14:
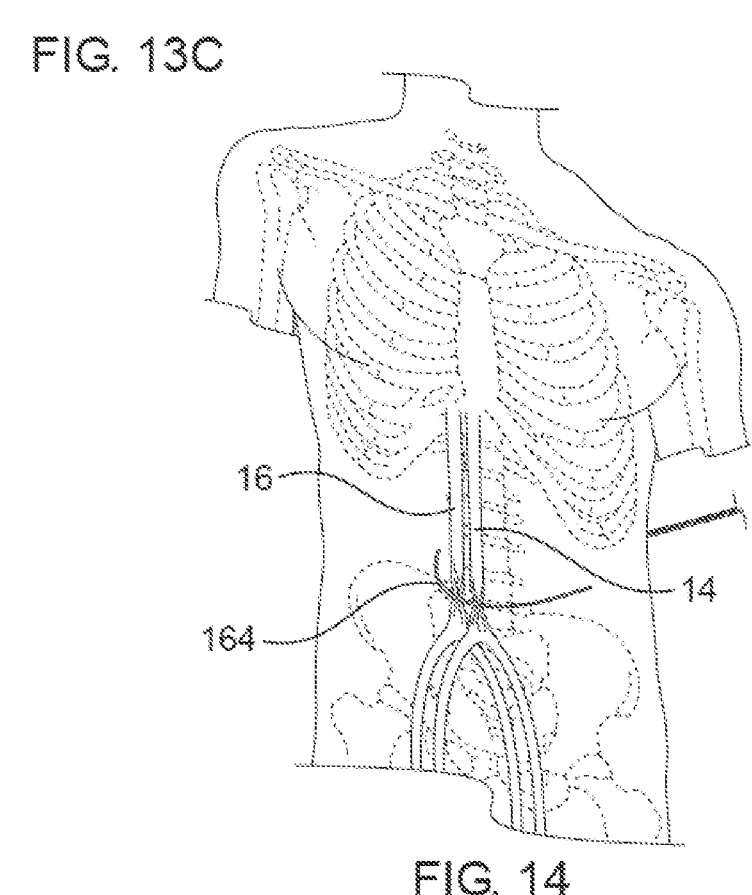
FIG. 14 shows the wire pulled and/or tensioned to collapse the abdominal aorta, according to some embodiments.

As further shown in FIG. 14, either proximally oriented retraction (in direction 52) of the wire 164 through first push shaft lumen 157a, while the proximal end of the wire 164 is kept in place to provide a counterforce, and/or rotation of the base plate 106ᵃ to twist both rear strands of the wire 164, causes the section of the wire 164 extending in front of the abdominal aorta 14, to be tightly and forcibly pulled against the abdominal aorta 14 and/or inferior vena cava 16, preferably collapsing these blood vessels between the wire 164 and the spine 10 in a manner that significantly reduces, and preferably halts, blood flow therethrough.

In some embodiments, the blood vessel compression apparatus 100ᵃ (or the portion of the apparatus 100ᵃ that remains attached to the patient) may be retained in this configuration until the patient arrives to an emergency facility, such as an operating room of a hospital, for further treatment. In some embodiments, the insertion device 102 may be partially (as described above) or completely (i.e., including the base plate) removable from the wire 164, allowing both ends of the wire 164 to be exposed from the patient's lower back, and optionally allowing these ends to be tightened together and retained in this position until the patient arrives to an emergency facility, such as an operating room of a hospital, for further treatment. In some embodiments, selected components of the insertion device 102 disposed externally to the patient, such as the handle assembly 138, the push member, the stopper, and the like, may be disconnected from the base plate 106 in a manner similar to that described above, allowing both ends of the wire 164 to be exposed from the base plate 106 and be similarly tightened over the base plate 106 instead of directly over the patient's skin.

Figure 15:
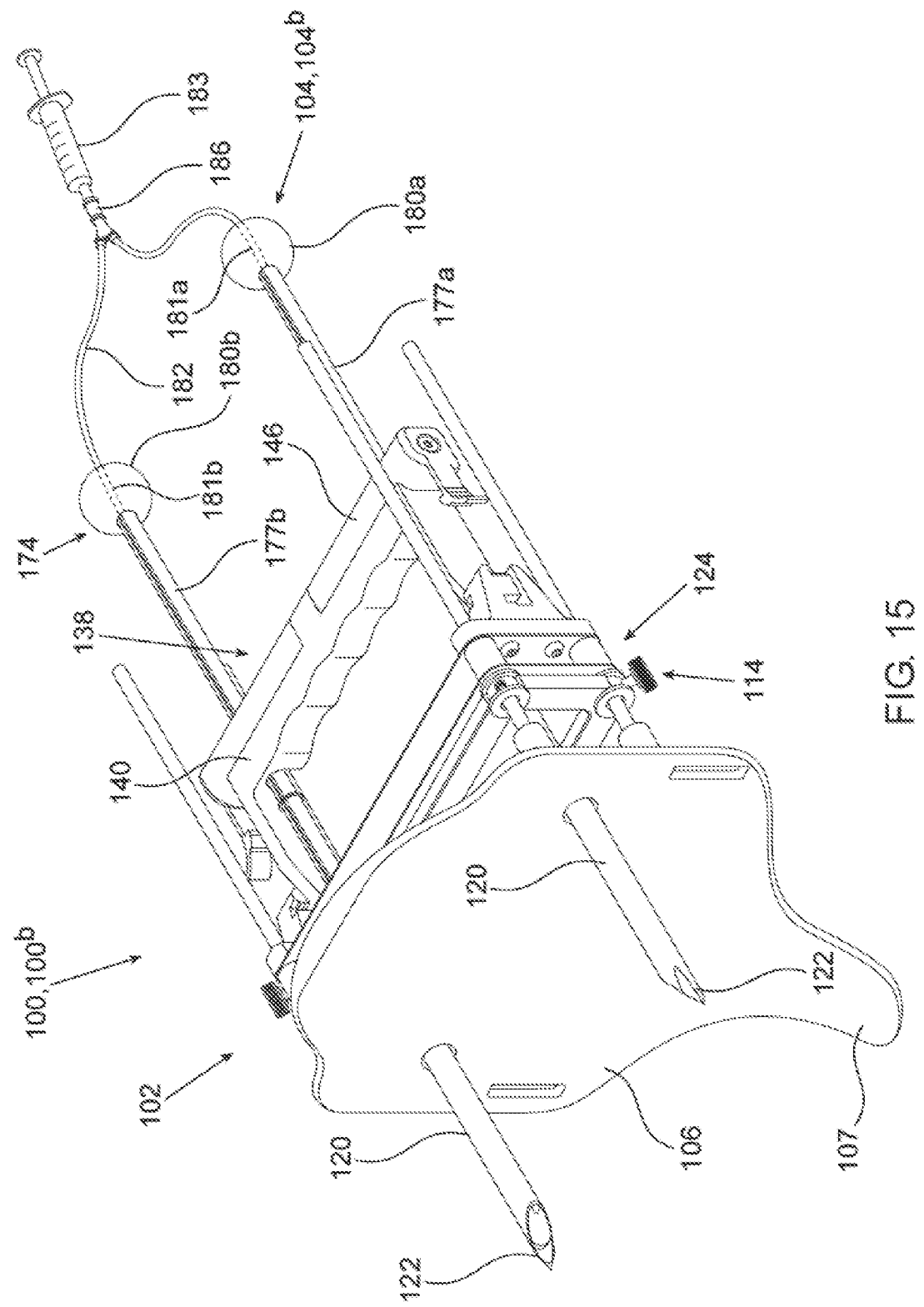
FIG. 15 shows a view in perspective of a blood vessel compression apparatus equipped with a balloon assembly having two balloon catheters, with the push shafts in a retained position, according to some embodiments.

FIG. 15 shows another embodiment of a blood vessel compression apparatus 100ᵇ, that includes the insertion device 102a according to any of the embodiments disclosed hereinabove, and a compression assembly 104ᵇ which, in some embodiments, includes a balloon assembly 174 instead of a wire with a wire retrieval assembly.

The balloon assembly 174 comprises at least one balloon catheter 177 defining a balloon catheter lumen 178, and carrying an inflatable balloon 179 attached thereto, at a distal portion of the balloon catheter 177. The balloon catheter is in fluid communications with a fluid source configured to contain inflation fluid (e.g., saline), that can be in some embodiments a syringe 183 utilized to inject the inflation fluid into the balloon 179 through the balloon catheter lumen 178, or a pump 184 for pumping the inflation fluid into balloon 179.

In some embodiments, an inflation tube 182 is fluidly connected between the fluid source (e.g., the syringe 183 or the pump 184) and the balloon catheter 177. In other embodiments, the balloon catheter 177 is directly connected to the syringe 183 or the pump 184.

In some embodiments, as illustrated in FIG. 15, the balloon assembly 174 of a compression assembly 104ᵇ comprises two balloon catheters carrying two inflatable balloons, such as the first balloon catheter 177a and the second balloon catheter 177b. In some embodiments, a single fluid source is fluidly connected to both balloon catheters 177a and 177b. For example, a single inflation tube 182 can be coupled to an outlet of fluid source, such as syringe 183 illustrated in FIG. 15, and then split into two branches—each coupled at its opposite end to one of the balloon catheters 177a and 177b. Alternatively, the fluid source itself, such as the pump 184 shown in FIG. 16, can be fluidly coupled to both balloon catheters 177a and 177b through two separate outlets, for example via two inflation tubes 182a and 182b.

In some embodiments, the balloon assembly 174 comprises at least one unidirectional valve 186, disposed within either at least one inflation tube 182 or at least one balloon catheter 177. A schematic example of a unidirectional valve 186 is shown in a zoomed in partial cross-sectional view in FIG. 18. The unidirectional valve 186 an be implemented as any one-way valve, configured to allow fluid flow through a lumen of the tube it is disposed in (i.e., the lumen of either inflation tube 182 or balloon catheter 177) in a distally oriented direction 50.

Figure 18:
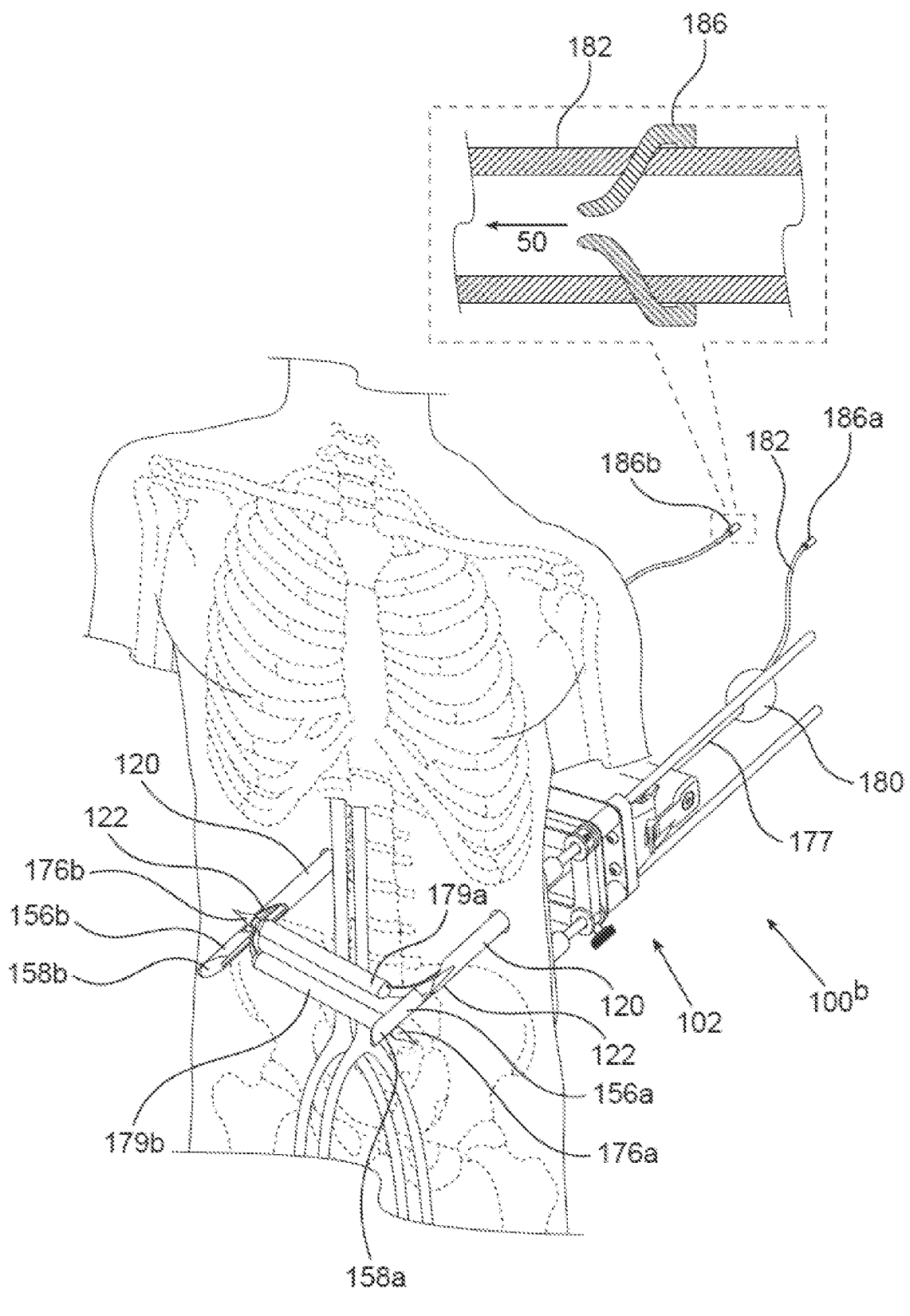
FIG. 18 shows a view in perspective of two deflated balloons extending in parallel to each other within the working space in front of the abdominal aorta, according to some embodiments.

It is to be understood that while shown in FIG. 18 to be disposed within the lumen of an inflation tube 182, and having a portion partially extending diametrically away from the inflation tube 182, this is shown for illustrative purpose only, and that in other implementation, the unidirectional valve 186 can be completely concealed within the lumen, can be disposed along one portion of an inflation tube 182 (see FIGS. 15-16) or two branching (or separate) inflation tubes 182 (see FIG. 18), can be disposed within a distal portion of an inflation tube 182 concealed within a balloon catheter 177, or can be disposed along any portion of the balloon catheter 177 (embodiments not shown).

Figure 16:
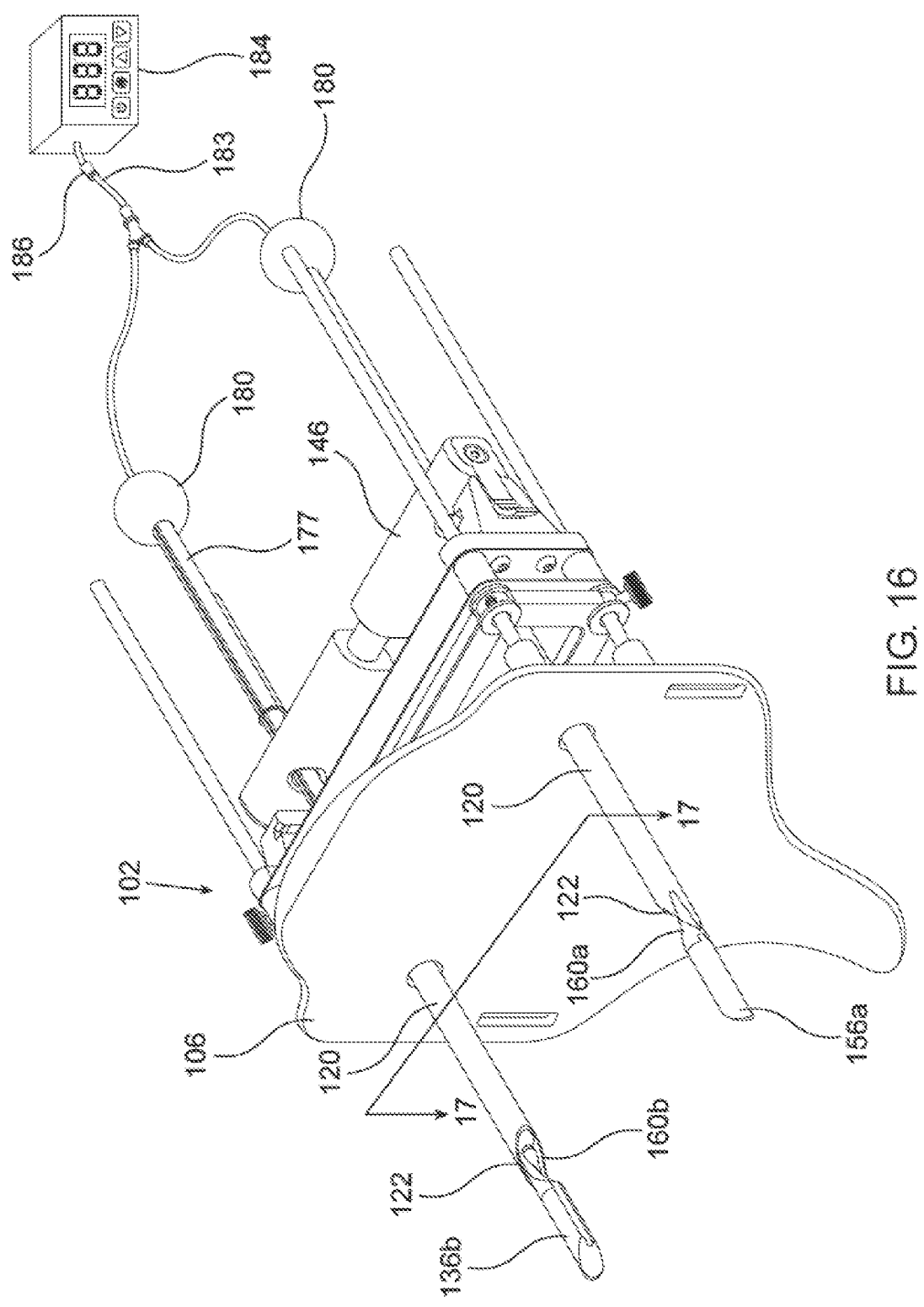
FIG. 16 shows a view in perspective of a blood vessel compression apparatus equipped with a balloon assembly, with the push shafts in a pushed position, according to some embodiments.
Figure 17:
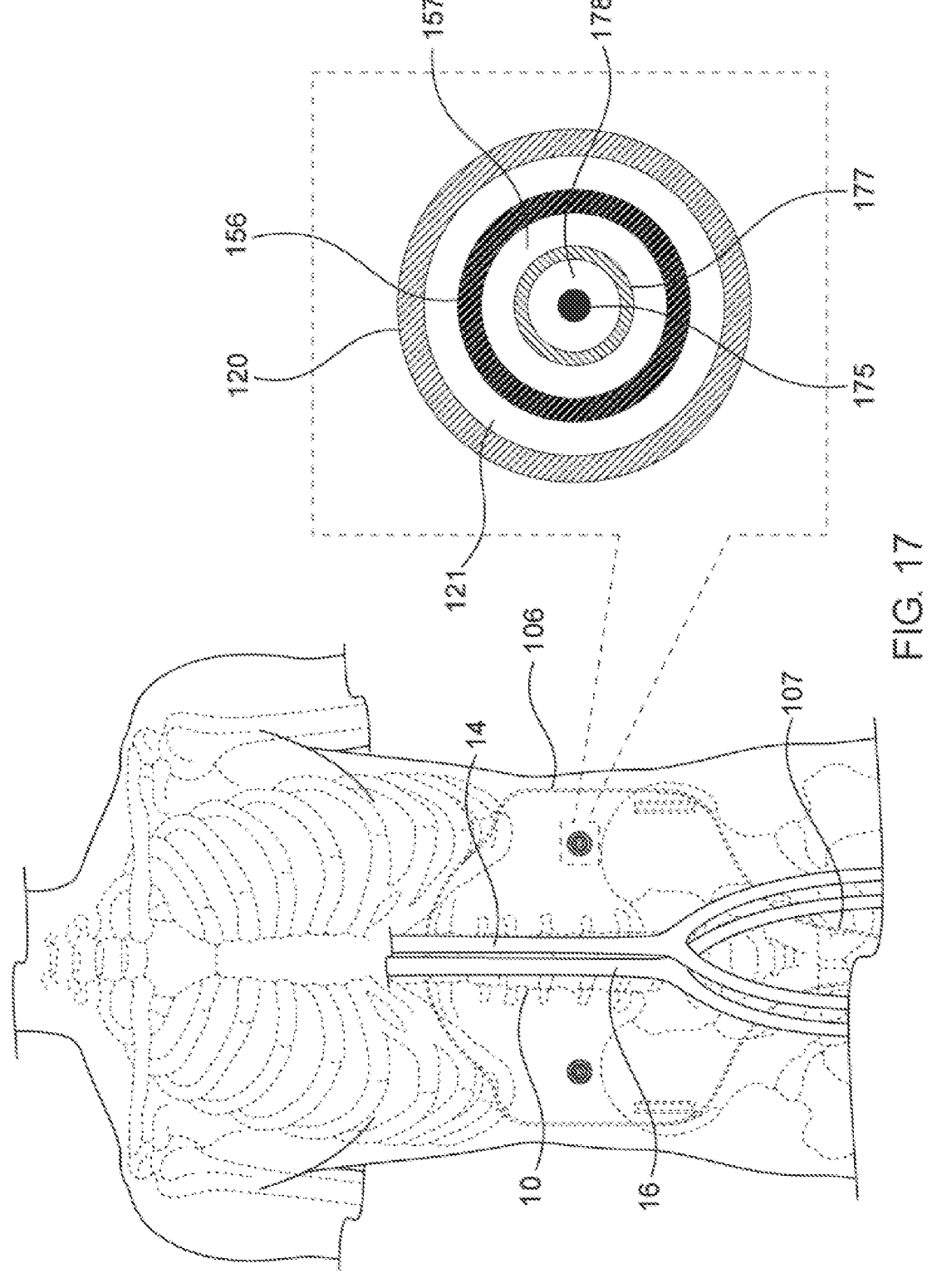
FIG. 17 schematically shows an anatomical front vie of a patient, with a cross-sectional zoomed-in view across lines 17-17 of FIG. 16.

The operation of insertion device $102^a$ in relation to blood vessel compression apparatus $100^b$ is in all respects similar to the operation of insertion device $102a$ in relation to blood vessel compression apparatus $100^a$, and in the interest of brevity will not be further described. For example, FIG. 16 shows the stage at which both push shafts 156a and 156b have been pushed distally, beyond the distal end 122 of the introducer shafts 120, so as to preferably push the peritoneum layer to form and maintain a working space into which the balloon catheters 177 may extend.

In some embodiments, at least one of the push shafts 156 includes a side opening 160 proximal to the atraumatic distal end 158, sized to allow the corresponding balloon catheter 177 and the inflatable balloon 179 attached thereto, to exit the push shaft lumen 157 into the working space. In some embodiments, each of both push shafts 156 of insertion device $102^a$ includes a side opening 160 sized to allow the corresponding balloon catheter 177 and the inflatable balloon 179 attached thereto, to exit there-through.

In some embodiments, balloon assembly 174 further comprises at least one nosecone 176 attached to the distal end of a corresponding balloon catheter 177, distally to the inflatable balloon 179, which can facilitate forward advancement of the balloon catheter 177. In some optional embodiments, balloon assembly 174 further comprises at least one guidewire 175 over which a corresponding balloon catheter 177 may be advanced. As shown in a cross-sectional zoomed-in view in FIG. 17, a push shaft 156 may be advanced through an introducer shaft lumen 121, and a balloon catheter 177 can be advanced in turn through the push shaft lumen 157, optionally over a guidewire 175 disposed within the balloon catheter lumen 178.

FIG. 18 an 19 show a view in perspective and a front view of blood vessel compression apparatus $100^b$ in a subsequent stage of utilization thereof. Once the push shafts 156 have been advanced distally to provide the desired working space, the balloon catheters 177 can be pushed distally until they reach side openings 160, at which point they may exit through side openings 160 and further extend laterally across the working space, each catheter 177 extending toward the opposite push shaft 156.

In some embodiments, balloon catheter 177 can be made of shape-memory materials, such as, but not limited to, nickel titanium alloy (e.g., Nitinol). When constructed of a shape-memory material, balloon catheter 177 can be pre-shaped to bend sideways and strive to exit through the corresponding side opening 160. Additionally or alternatively, guidewire 175 can be made of shape-memory materials, such as, but not limited to, nickel titanium alloy (e.g., Nitinol). When constructed of a shape-memory material, guidewire 175 can be pre-shaped to bend sideways and strive to exit through the corresponding side opening 160, serving as a guiding member over which the corresponding balloon catheter 177 can follow and exit through the same side opening 160 laterally toward the opposite push shaft 156. Additionally or alternatively, the corresponding push shaft lumen 157 can terminate with a deflecting edge (similar to deflecting edge 161) at the level of the side opening 160, such as proximate to its distal end, which can be in the form of an angled surface configured to deflect guidewire 175 and/or balloon catheter 177, through the corresponding side opening 160.

Figure 19:
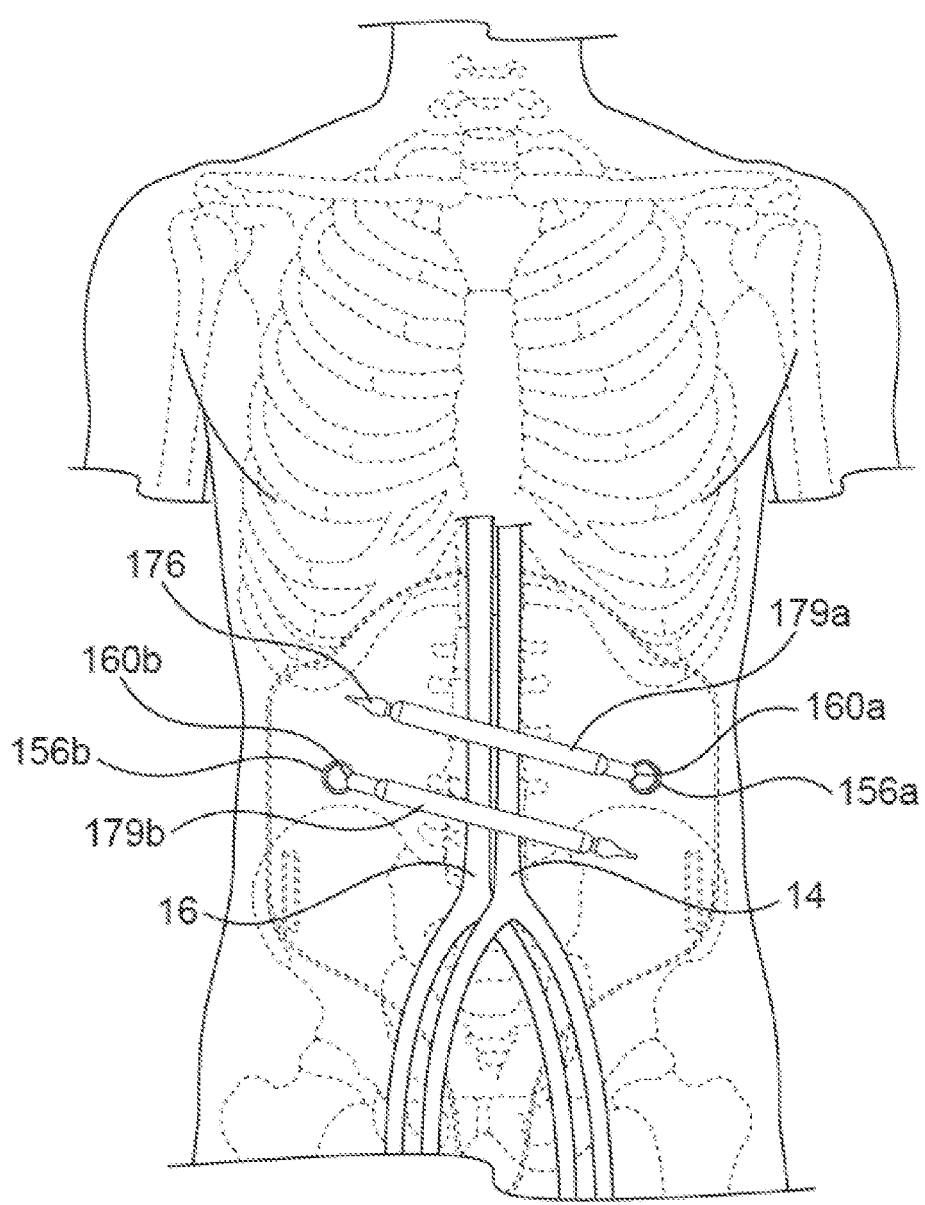
FIG. 19 shows a front view of the balloons of shown in FIG. 18, according to some embodiments.

In some embodiments, as shown in FIGS. 18-19 for a balloon assembly 174 of compression assembly $104^b$ comprising two balloon catheters 177, both side opening 160 are angularly offset from each other, such that each side opening 160 is facing the opposite side opening 160 at a non-zero angle, meaning that each side opening 160 is angularly oriented at a non-zero angle with respect to an axis (not shown) extending between both side openings 160. In this manner, both balloon catheters 177 carrying inflatable balloons 179 extend laterally to the push shafts 156 at an angle such that the extended portions do not interfere with each other (at least in a deflated state of the balloons 179), as shown. Both balloon catheters 177 carrying inflatable balloons 179 can be parallel to each other when fully extended.

In some additional embodiments (not shown), both introducer shafts 120 and push shafts 156 extending therethrough may be un-aligned vertically with respect to each other, such that one push shaft may be vertically higher (or lower) than its counterpart. In this manner, both side openings 160 can be also oriented sideways at a zero-angle, wherein the height difference may be set to ensure that both balloon catheters 177 carrying inflatable balloons 179 extend laterally through the side opening 160 one above the other, without interfering with each other (at least in a deflated state of the balloons 179).

In some embodiments, balloon assembly 174 further comprises at least one catheter proximal stopping portion 180 attached to a proximal portion of a corresponding balloon catheter 177, and disposed proximal to the second stage handle 146. The catheter proximal stopping portion 180 has a size larger than that of the corresponding push shaft lumen 157 and/or a channel or proximal opening of the second stage handle 146 aligned therewith. While catheter proximal stopping portions 180 in the form of enlarged beads or ball-shaped members are illustrated, it is to be understood that other shapes are contemplated. Each catheter proximal stopping portion 180 can further define a stopping portion channel 181 which is in fluid communication with the balloon catheter lumen 178, allowing inflation fluid to flow therethrough into the balloon catheter lumen 178 toward the balloon 179.

In some embodiments, the balloon catheter 177 is advanced until the catheter proximal stopping portion 180 is stopped, for example by the second stage handle 146. The extent of advancement is proportional to the distance of the catheter proximal stopping portion 180 from the second stage handle 146 in such cases, and may be set to allow full extension of the corresponding inflatable balloon 179 out of the push shaft lumen 157, but preferably not beyond the position of the opposite push shaft 156, as illustrated.

Figure 20:
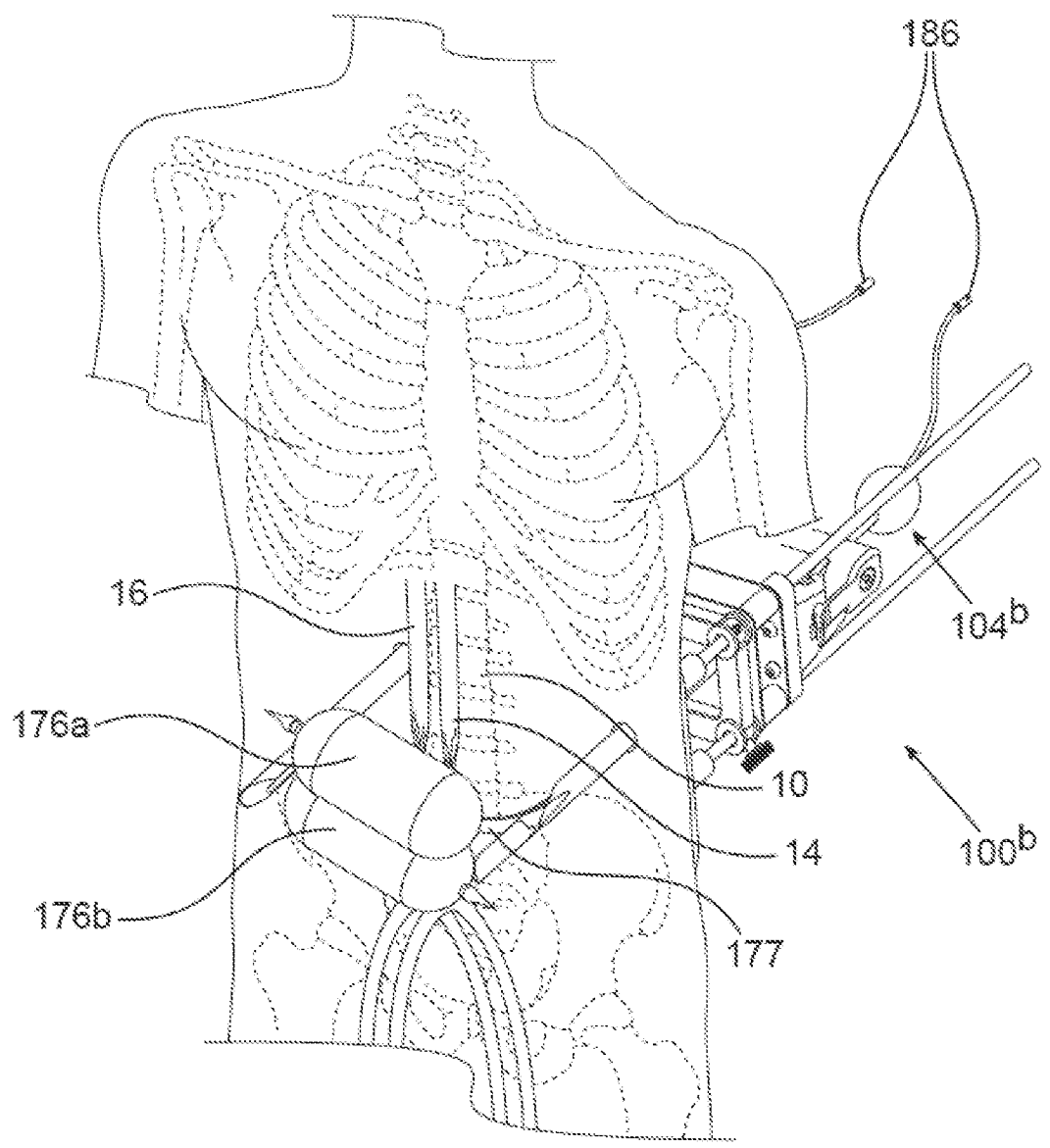
FIG. 20 shows a view in perspective of two balloons inflated to press against and collapse the abdominal aorta, according to some embodiments.

FIG. 20 schematically shows a subsequent stage of a method for utilizing a blood vessel compression apparatus $100^b$, wherein the inflatable balloons 179 are inflated by injection inflation fluid there-into. The distance to which any of the balloon 179 extends out of the push shaft 156 in its deflated, yet extended state (i.e., disposed within the working space), and the balloon's diameter when fully inflated, are configured to allow the balloons to forcibly press against the abdominal aorta 14 and/or inferior vena cava 16 upon inflation, preferably collapsing these blood vessels between the balloons 179 and the spine 10 in a manner that significantly reduces, and preferably halts, blood flow therethrough.

Figure 21:
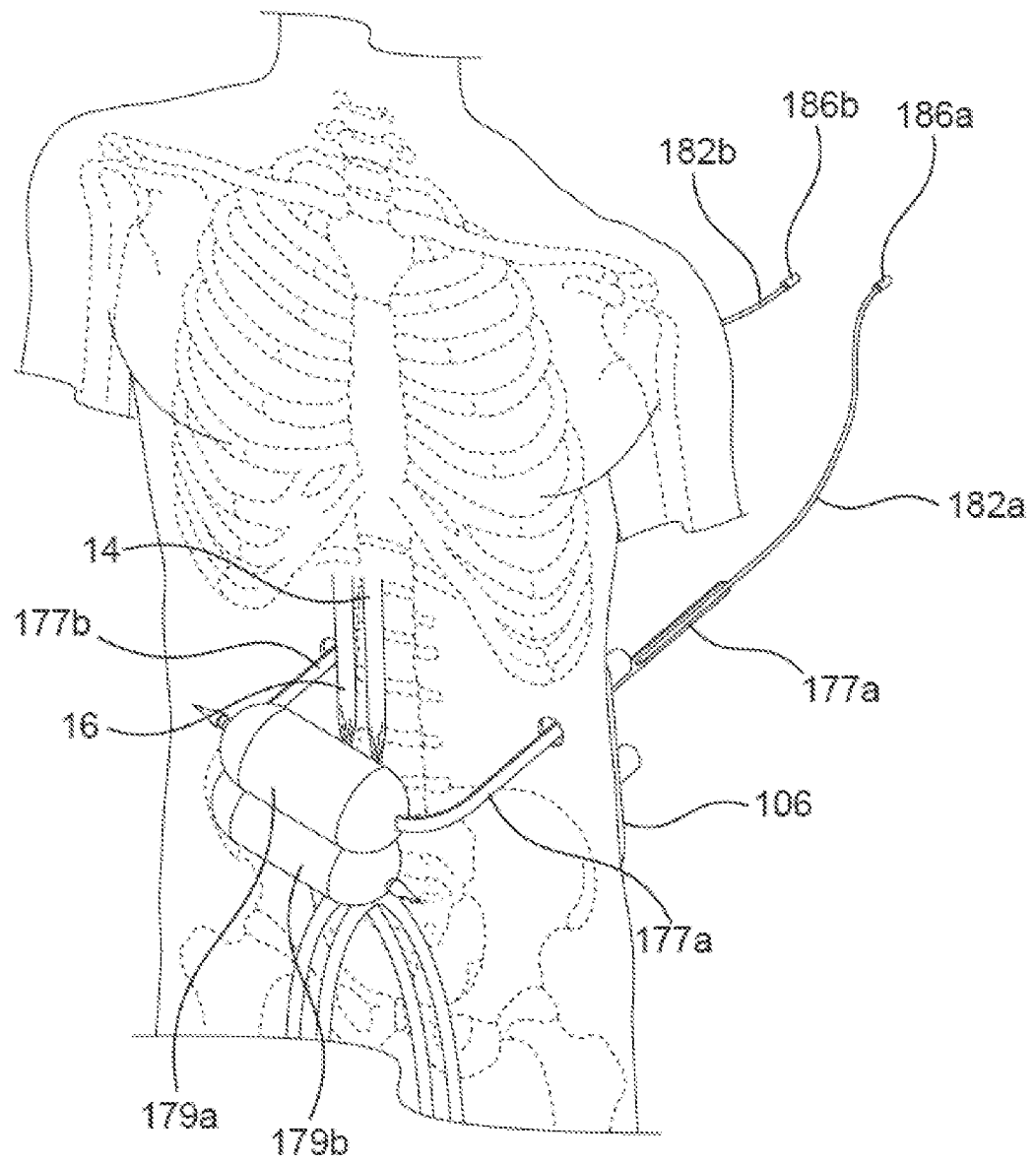
FIG. 21 shows a view in perspective of the balloons inflated against the blood vessels, with components of the blood vessel compression apparatus decoupled and removed, according to some embodiments.

In some embodiments, portions of the blood vessel compression apparatus $100^b$, including selected components of the compression assembly $104^b$ and/or the insertion device $102^a$ can be pulled away and removed, similar to removal thereof as described above with respect to blood vessel compression apparatus $100^a$. FIG. 21 illustrates all components of the insertion device $102^a$ except the base plate 106 removed, which is shown for illustrative purpose only, as less or more components (including the base plate 106) can be selectively removed. Moreover, the balloon catheters 177, optionally with the inflation tubes 182, can be decoupled from the fluid source (such as syringe 183 or pump 184), wherein unidirectional valve 186 may retain the balloon 179 in an inflated state, and prevent backflow of the inflation fluid.

A portion of the balloon catheter 177, extending proximally from the patient's back, is illustrated in partial sectional view to illustrate an example in which the corresponding inflation tube 182 partially extends through and into the balloon catheter lumen 178. It is to be understood that in other implementations, an inflation tube 182 can be coupled to the proximal end of a corresponding balloon catheter 177 without extending into its lumen, and in yet other implementations, the balloon assembly 174 may include a balloon catheter 177 without any inflation tube.

Figure 22:
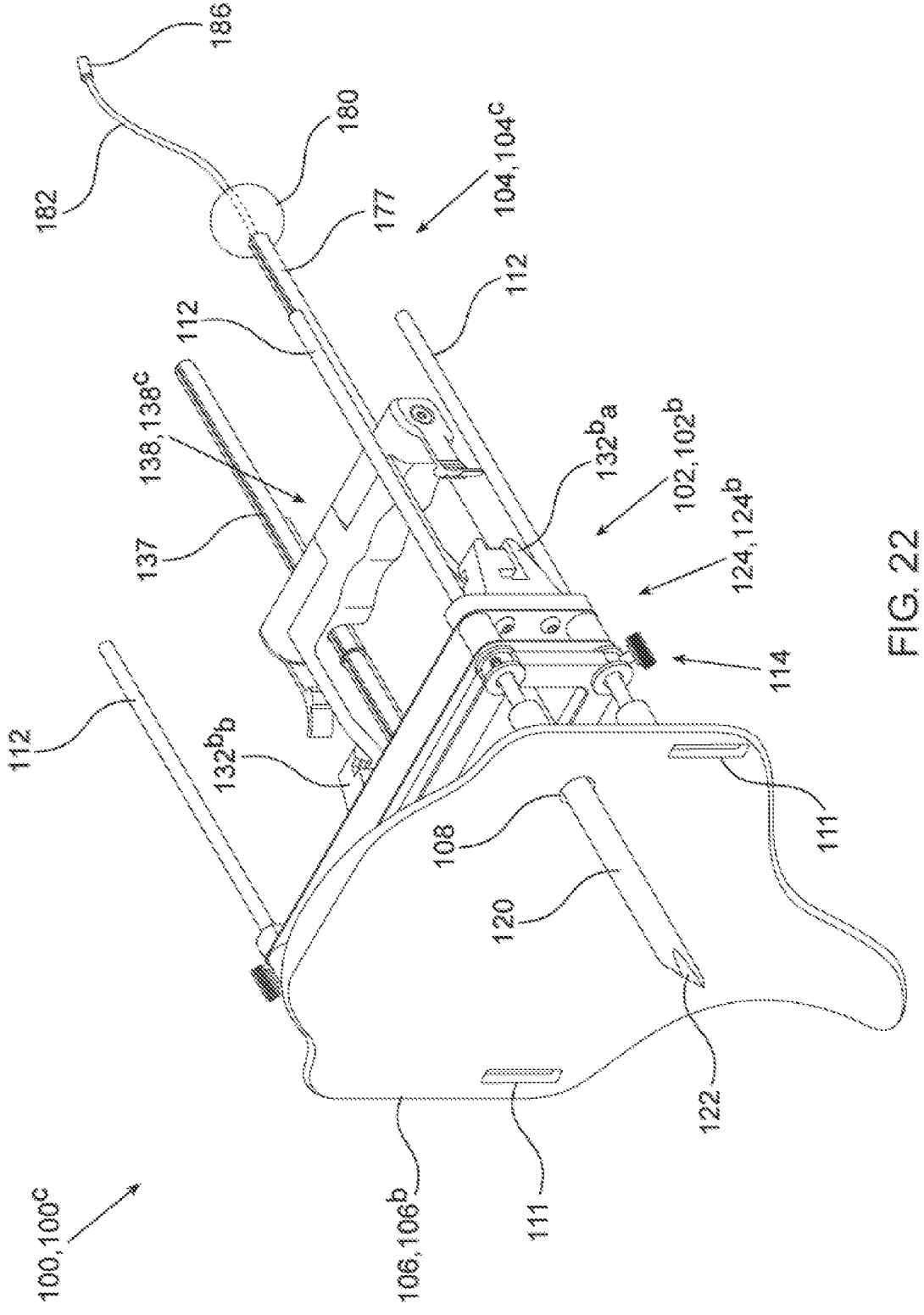
FIG. 22 shows a view in perspective of a blood vessel compression apparatus equipped with a balloon assembly having a single balloon catheter, according to some embodiments.
Figure 23:
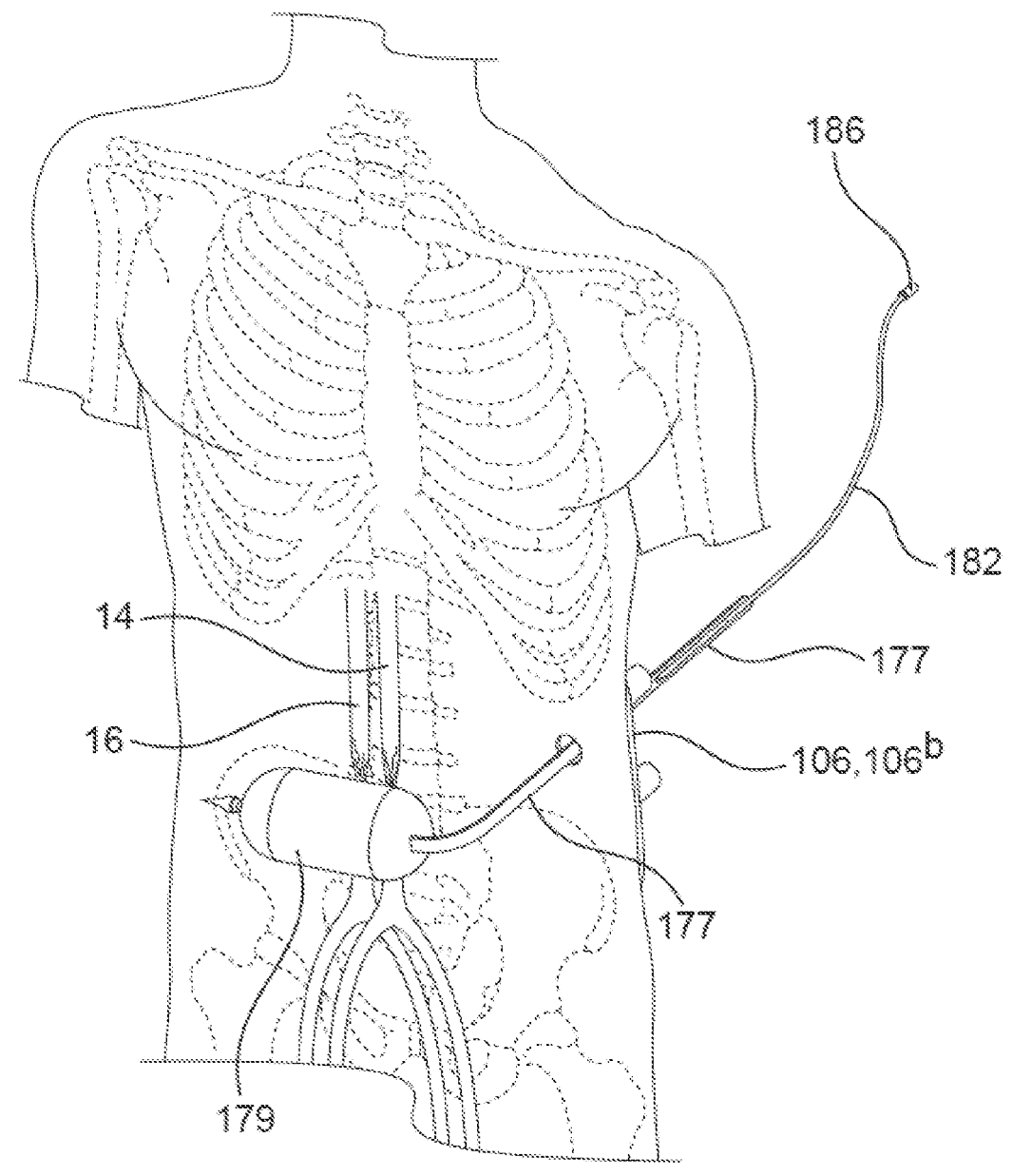
FIG. 23 shows a view in perspective of a single balloon inflated against the blood vessels, with components of the blood vessel compression apparatus decoupled and removed, according to some embodiments.

While FIGS. 15-21 illustrate a blood vessel compression apparatus 100$^b$ comprising compression assembly 100$^b$ with two balloon catheters 177 carrying two inflatable balloons 179, this is not meant to be limiting in any way. FIGS. 22-23 illustrate another embodiment of a blood vessel compression apparatus 100$^c$ comprising an insertion device 102$^b$ and a compression assembly 100$^b$. As shown in FIG. 22, compression assembly 100$^b$ is similar to compression assembly 104$^a$, with the exception that its balloon assembly 174 comprises a single balloon catheter 177 carrying a single inflatable balloon 179. Similarly, the insertion device 102$^b$ is similar to insertion device 102$^a$, except that it includes a single introducer shaft 120 axially movable through a single base plate opening 108 of base plate 106$^b$, and a single push shaft 156 movable through the lumen of the single introducer shaft 120.

The operation of blood vessel compression apparatus 100$^c$ is similar to that described above for blood vessel compression apparatus 100$^b$, mutatis mutandis. Specifically, the balloon catheter 177 can be similarly advanced through the single push shaft lumen 157 and extend through the corresponding side opening 160 laterally into the working space created by the push shaft 156 pushing against the peritoneum. In case only a single push shaft 156 of an insertion device 102$^b$ is utilized to push against the peritoneum on only one side of the abdominal aorta 14, a "tent"-like configuration may result for the working space, distancing the peritoneum forward at the position of the push shaft 156, yet angled back to its original position on the opposite side which is devoid of a push shaft. Nevertheless, since the balloon assembly 174 can be equipped with a nosecone 176, as long as the working space is sufficient to extend the nosecone 176 thereinto, applying additional push force on the balloon catheter 177 will push the nosecone (optionally over guidewire 175) to facilitate advancement of the balloon 179 to extend in front and across the abdominal aorta 14 and/or the inferior vena cava 16.

The introducer push member of the insertion device 102$^b$ can be implemented according to any of the embodiments described above for push members 124, 224 or 324 in conjunction with insertion device 102$^a$. The stopper of the insertion device 102$^b$ can be implemented according to any of the embodiments described above for stoppers 114, 214 or 314 in conjunction with insertion device 102$^a$.

The size and shape of base plate 106$^b$ can be similar to that of push plate 106$^a$, that is—being sized and shaped for convenient placement over the patient's back. However, the handle assembly 138$^b$ of insertion device 102$^b$ can be either identical in size as that illustrated for insertion device 102$^a$, or shorter in the lateral direction (as illustrated in FIG. 22), in which case either the push member and/or stopper of the insertion device 102$^b$ can be similarly provided with a smaller size (mainly shorter in the lateral direction), as it is not required to extend over a push member opposite to the single push shaft 156 of the insertion device 102$^b$.

In some embodiments, the insertion device 102$^b$ further comprises a handle support rod (or tube) 137, which may extend proximally from the introducers push member 124$^b$ and through openings of the handle assemble 138$^b$, to provide support over which the handle assemble 138$^b$ may slide instead of the missing opposite push shaft.

FIG. 23 shows a final optional configuration of a single balloon 179 inflated so as to forcibly press against the abdominal aorta 14 and/or inferior vena cava 16, wherein components of the blood vessel compression apparatus 100$^c$ can be pulled and removed in the same manner described above in conjunction with FIG. 21. In some embodiments, unlike the configuration shown in FIGS. 19-21, the side opening 160 does not need to be angled, such that the balloon 179 can extend laterally (i.e., at a zero angle) sideways, across the abdominal aorta 14 and/or inferior vena cava 16, since in this case there is no risk of two balloons extending toward each other.

While not shown explicitly, another type of a blood vessel compression apparatus 100 can comprise an insertion device 102$^a$ that includes two introducer shafts 120 with two push shafts 156, and a compression assembly 100$^b$ that includes a single balloon catheter 177 carrying a single balloon 179, extendable through the lumen 157 of one push shaft 156 while the opposite push shaft can either include a lumen or not. In such embodiments, the single balloon catheter 177 can extend through the corresponding side opening 160 toward the opposite push shaft. In such embodiments (not illustrated), utilization of two push shafts 156 (movable through two corresponding introducer shafts 120), even when only a single balloon 179 is utilized, can be advantageous to properly push the peritoneum layer along both sides of the spine 10 and abdominal aorta 14, to form a working space into which the balloon 179 can extend more easily, without interference or obstruction across the abdominal aorta 14 (if, for example, a nosecone is not utilized or does not provide the required push force).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although the invention is described in conjunction with specific embodiments thereof, it is evident that numerous alternatives, modifications and variations that are apparent to those skilled in the art may exist. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The invention claimed is:

1. A blood vessel compression apparatus comprising an insertion device, the insertion device comprising:

a base plate comprising two base plate openings which are laterally spaced from each other;

two introducer shafts which are axially movable through the base plate openings, wherein each of the introducer shaft defines an introducer shaft lumen and comprises a sharp distal end;

at least one guide member, affixed to the base plate and extending proximally therefrom;

a push member, axially slidable over the at least one guide member;

a first push shaft and a second push shaft, wherein each of the push shafts is axially movable through the corresponding introducer shaft lumen, wherein each of the push shafts comprises an atraumatic distal end, wherein first push shaft defines a first push shaft lumen and comprises a first side opening which is proximal to an atraumatic distal end of the first push shaft, and wherein the second push shaft defines a second push shaft lumen and comprises a second side opening proximal to an atraumatic distal end of the second push shaft;

a handle assembly coupled to the push member, the handle assembly comprising a first stage handle and a second stage handle, wherein the first stage handle is coupled to the second stage handle; and a compression assembly comprising a wire and a wire retrieval assembly, the wire retrieval assembly comprising a snare loop configured to transition between a compressed state and an expanded state;

wherein the introducer shafts are attached to the push member and are axially movable therewith;

wherein the push shafts are attached to the second stage handle and are axially movable therewith; and wherein the push shafts are movable between a retained position, in which the atraumatic distal ends are retained within the introducer shaft lumens, and a pushed position, in which the atraumatic distal ends protrude distally from the sharp distal ends; and wherein the wire extends at least partially through the second push shaft lumen, and the wire retrieval assembly extends at least partially through the first push shaft lumen.

2. The blood vessel compression apparatus of claim 1, wherein the push member comprises at least one guide channel, and wherein each guide member extends through a corresponding guide channel.

3. The blood vessel compression apparatus of claim 1, wherein the push member comprises push plate.

4. The blood vessel compression apparatus of claim 1, further comprises at least one stopper coupled to the at least one guide member, and configured to prevent axial advancement of the push member along the at least one guide member beyond the at least one stopper.

5. The blood vessel compression apparatus of claim 1, wherein the first stage handle is rotatably coupled to the second stage handle.

6. The blood vessel compression apparatus of claim 1, wherein the first stage handle is releasably coupled to the second stage handle.

7. The blood vessel compression apparatus of claim 1, wherein the wire retrieval assembly further comprises a longitudinal portion extending proximally from the snare loop, and movable axially within the first push shaft lumen.

8. The blood vessel compression apparatus of claim 7, wherein the longitudinal portion is configured to extend proximally out of the first push shaft, and comprises a retrieval proximal stopping portion disposed proximal to the second stage handle, the retrieval proximal stopping portion sized to be larger than the first push shaft lumen.

9. The blood vessel compression apparatus of claim 1, wherein the first side opening is facing upward or downward with respect to a longitudinal axis defined by the first push shaft.

10. The blood vessel compression apparatus of claim 1, wherein the first side opening comprises two opposing openings, one facing upward and the other facing downward with respect to a longitudinal axis defined by the first push shaft.

11. The blood vessel compression apparatus of claim 1, wherein the snare loop comprises a shape memory material and is pre-shaped to self-expand through the first side opening.

12. The blood vessel compression apparatus of claim 1, wherein the wire comprises a shape memory material and is pre-shaped to bend sideways from the second push shaft lumen through the second side opening, toward the first push shaft.

13. A blood vessel compression apparatus comprising an insertion device, the insertion device comprising:

a base plate comprising two base plate openings which are laterally spaced from each other;

two introducer shafts which are axially movable through the base plate openings, wherein each of the introducer shaft defines an introducer shaft lumen and comprises a sharp distal end;

at least one guide member, affixed to the base plate and extending proximally therefrom;

a push member, axially slidable over the at least one guide member;

two push shafts axially movable through the introducer shaft lumens, wherein each of the push shafts comprises an atraumatic distal end, and wherein each of the push shafts defines a push shaft lumen and comprises a side opening which is proximal to the corresponding atraumatic distal end;

a handle assembly coupled to the push member, the handle assembly comprising a first stage handle and a second stage handle, wherein the first stage handle is coupled to the second stage handle; and a compression assembly comprising a balloon assembly, the balloon assembly comprising: two balloon catheters, each balloon catheter defining a balloon catheter lumen, and two inflatable balloons, each balloon attached to one of the balloon catheters;

wherein the introducer shafts are attached to the push member and are axially movable therewith;

wherein the push shafts are attached to the second stage handle and are axially movable therewith;

wherein the push shafts are movable between a retained position, in which the atraumatic distal ends are retained within the introducer shaft lumens, and a pushed position, in which the atraumatic distal ends protrude distally from the sharp distal ends; and wherein each balloon catheter extends at least partially through the push shaft lumen of the corresponding push shaft.

14. The blood vessel compression apparatus of claim 13, wherein the balloon catheters comprise shape memory materials, and are pre-shaped to bend sideways through the side openings of the corresponding push shafts.

15. The blood vessel compression apparatus of claim 13, wherein the balloon assembly further comprises at least one catheter proximal stopping portion attached to a proximal portion of at least one of the balloon catheters, the at least one catheter proximal stopping portion disposed proximal to the second stage handle and sized to be larger than the corresponding push shaft lumen.

16. The blood vessel compression apparatus of claim 13, wherein the side openings of both push shafts are facing each other at a non-zero angle.

17. A blood vessel compression apparatus of comprising an insertion device, the insertion device comprising:

a base plate comprising a single plate opening;

a single introducer shaft axially movable through the base plate opening, wherein the introducer shaft defines an introducer shaft lumen and comprises a sharp distal end;

at least one guide member, affixed to the base plate and extending proximally therefrom;

a push member, axially slidable over the at least one guide member;

a single push shaft movable through the introducer shaft lumen, wherein the push shafts comprises an atraumatic distal end, and wherein the push shafts defines a push shaft lumen and comprises a side opening which is proximal to the atraumatic distal end;

a handle assembly coupled to the push member, the handle assembly comprising a first stage handle and a second stage handle, wherein the first stage handle is coupled to the second stage handle; and a compression assembly comprising a balloon assembly, wherein the balloon assembly comprises a single balloon catheter which defines a balloon catheter lumen, and an inflatable balloon attached to the balloon catheter;

wherein the introducer shaft is attached to the push member and is axially movable therewith;

wherein the push shaft is attached to the second stage handle and is axially movable therewith;

wherein the push shaft is movable between a retained position, in which the atraumatic distal end is retained within the introducer shaft lumen, and a pushed position, in which the atraumatic distal end protrudes distally from the sharp distal end; and wherein the balloon catheter extends at least partially through the push shaft lumen.

18. The blood vessel compression apparatus of claim 17, wherein the balloon catheter comprises a shape memory material, and is pre-shaped to bend sideways through the side opening of the push shaft.

* * * * *